(12) United States Patent
Gogarty et al.

(10) Patent No.: US 11,154,372 B2
(45) Date of Patent: Oct. 26, 2021

(54) ROBOTIC CUTTING WORKFLOW

(71) Applicant: Orthosoft ULC, Montreal (CA)

(72) Inventors: Emily Gogarty, Montreal (CA); Olivier Boisvert, Montreal (CA); Pierre Couture, Montreal (CA); Di Li, LaSalle (CA); Benoit Pelletier, Laval (CA); Jean-Sebastien Merette, Mont-St-Hiliare (CA); Suntara Ly, Longueuil (CA)

(73) Assignee: Orthosoft ULC, Montreal (CA)

( * ) Notice: Subject to any disclaimer, the term of this patent is extended or adjusted under 35 U.S.C. 154(b) by 653 days.

(21) Appl. No.: 15/795,019

(22) Filed: Oct. 26, 2017

(65) Prior Publication Data

US 2018/0116739 A1    May 3, 2018

Related U.S. Application Data

(60) Provisional application No. 62/414,033, filed on Oct. 28, 2016.

(51) Int. Cl.
*A61B 34/32* (2016.01)
*A61B 34/30* (2016.01)
(Continued)

(52) U.S. Cl.
CPC .......... *A61B 34/32* (2016.02); *A61B 17/1703* (2013.01); *A61B 34/10* (2016.02); *A61B 34/20* (2016.02); *A61B 34/30* (2016.02); *B25J 9/1689* (2013.01); *B25J 9/1697* (2013.01); *A61B 17/154* (2013.01); *A61B 17/155* (2013.01); *A61B 17/157* (2013.01); *A61B 17/175* (2013.01); *A61B 17/1764* (2013.01); *A61B 34/25* (2016.02); *A61B 90/11* (2016.02); (Continued)

(58) Field of Classification Search
CPC ..................................................... A61B 34/32
See application file for complete search history.

(56) References Cited

U.S. PATENT DOCUMENTS 7,035,716 B2   4/2006   Harris et al.
9,639,156 B2   5/2017   Iorgulescu et al.
(Continued)

FOREIGN PATENT DOCUMENTS

CN    110114031    8/2019

OTHER PUBLICATIONS

"Australian Application Serial No. 2017348662, First Examination Report dated Jun. 26, 2019", 2 pgs.
(Continued)

*Primary Examiner* — Nicholas W Woodall
(74) *Attorney, Agent, or Firm* — Schwegman Lundberg & Woessner, P.A.

(57) ABSTRACT

Embodiments of a system and method for surgical tracking and control are generally described herein. A system may include a robotic arm configured to allow interactive movement and controlled autonomous movement of an end effector, a cut guide mounted to the end effector of the robotic arm, the cut guide configured to guide a surgical instrument within a plane, a tracking system to determine a position and an orientation of the cut guide, and a control system to permit or prevent interactive movement or autonomous movement of the end effector.

14 Claims, 17 Drawing Sheets

(51) Int. Cl.
*A61B 34/10* (2016.01)
*A61B 34/20* (2016.01)
*A61B 17/17* (2006.01)
*B25J 9/16* (2006.01)
*A61B 90/00* (2016.01)
*A61B 17/15* (2006.01)
*A61B 90/11* (2016.01)
*A61B 34/00* (2016.01)
*A61B 17/00* (2006.01)

(52) U.S. Cl.
CPC ............... *A61B 2017/00022* (2013.01); *A61B 2017/00199* (2013.01); *A61B 2034/104* (2016.02); *A61B 2034/105* (2016.02); *A61B 2034/107* (2016.02); *A61B 2034/207* (2016.02); *A61B 2034/2055* (2016.02); *A61B 2034/2057* (2016.02); *A61B 2034/254* (2016.02); *A61B 2090/064* (2016.02); *A61B 2090/066* (2016.02); *A61B 2090/365* (2016.02); *G05B 2219/40146* (2013.01); *G05B 2219/45117* (2013.01)

(56) References Cited

U.S. PATENT DOCUMENTS

| | | | | |
|---|---|---|---|---|
| 2005/0171545 | A1* | 8/2005 | Walsh | A61B 17/154 128/898 |
| 2006/0064105 | A1* | 3/2006 | Raistrick | A61B 17/154 606/87 |
| 2006/0142657 | A1* | 6/2006 | Quaid | A61B 17/1675 600/424 |
| 2007/0156157 | A1* | 7/2007 | Nahum | A61B 17/154 606/130 |
| 2011/0130761 | A1 | 6/2011 | Plaskos et al. | |
| 2015/0202014 | A1 | 7/2015 | Kim et al. | |
| 2015/0245879 | A1* | 9/2015 | Nikou | A61B 17/155 606/88 |
| 2018/0116740 | A1 | 5/2018 | Gogarty et al. | |

OTHER PUBLICATIONS

Ortmaier, T., et al., "A Hands-On-Robot for Accurate Placement of Pedicle Screws", Proceedings of the 2006 IEEE International Conference on Robotics and Automation, (May 2006), p. 4179-4186.

"International Application Serial No. PCT CA2017 051277, International Search Report dated Feb. 2, 2018", 3 pgs.

"International Application Serial No. PCT CA2017 051277, Written Opinion dated Feb. 2, 2018", 4 pgs.

"U.S. Appl. No. 15/795,029, Restriction Requirement dated Oct. 23, 2019", 6 pgs.

"U.S. Appl. No. 15/795,029, Non Final Office Action dated Mar. 5, 2020", 8 pgs.

"U.S. Appl. No. 15/795,029, Response filed Jun. 5, 2020 to Non Final Office Action dated Mar. 5, 2020", 9 pgs.

"U.S. Appl. No. 15/795,029, Response filed Dec. 18, 2019 to Restriction Requirement dated Oct. 23, 2019", 7 pgs.

"Canadian Application Serial No. 3,042,097, Office Action dated May 5, 2020", 4 pgs.

* cited by examiner

ROBOTIC CUTTING WORKFLOW

CLAIM OF PRIORITY

This application claims the benefit of U.S. Provisional Patent Application Ser. No. 62/414,033, filed on Oct. 28, 2016, the benefit of priority of which is claimed hereby, and which is incorporated by reference herein in its entirety.

BACKGROUND

A guide is used in surgery to align a cutting, burring, or sawing device with a target object. A cut guide is useful for planning out a cut and allowing for the cut to be precise even in the presence of vibration or movement of the cutting device. However, the cut guide is sometimes placed imprecisely due to patient movement, lack of experience, or obstructed visual access.

The use of robotics in surgery is on the rise as more procedures are using robotics to positively affect surgical outcomes. While techniques using robotics to control surgical tools such as cutting devices, these techniques sometimes come with high costs, specialized equipment, longer surgical planning times, or longer surgical operation times.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
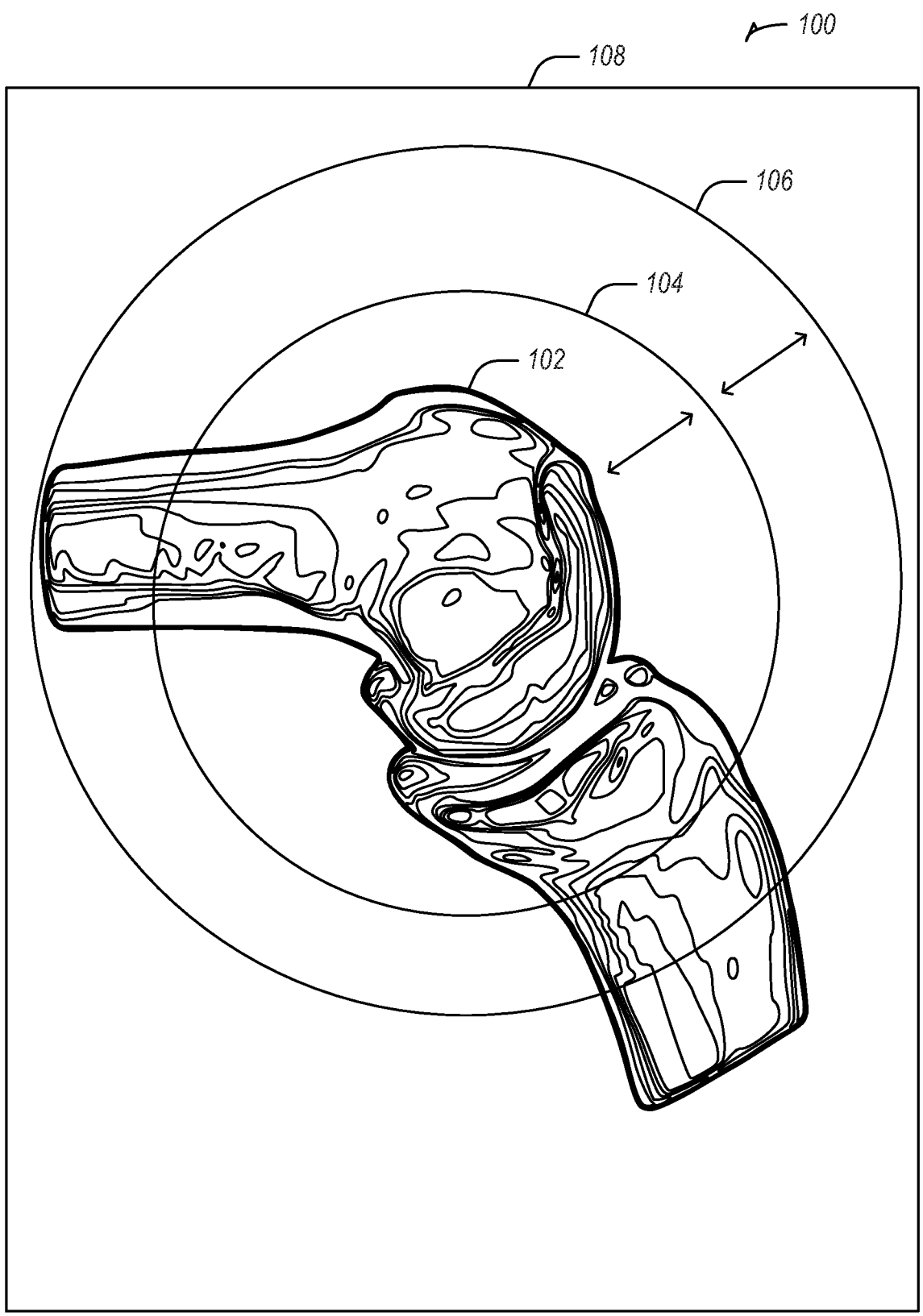
FIG. 1 illustrates a system including a target object and a plurality of zones in accordance with some embodiments.

As discussed above, a guide may be used to align a cutting, burring, or sawing device with a target object, such as a target bone. Cut guides are often manually placed by a surgeon on the target object. In other examples, cuts are made using fully autonomous robotic cutting devices. The systems and techniques described herein use a robotic arm to control a robotic end effector including a cut guide, burr guide, or saw guide. The robot provides fast accurate positioning of the robotic end effector allowing the surgeon to focus on completing the procedure with minimal impact on the patient.

Systems and methods for surgical tracking and control are described herein. The robotic arm may be used in a surgical field, such as for total knee arthroplasty, hip replacement, etc. In an example, the cut guide may be used to precisely align a surgical instrument to make a cut, such as on a target bone or other target object. The alignment of the robotic end effector may involve a planning system with a user interface including positioning a representation of the robotic end effector on a representation of the target object. During the surgical procedure, a selectable indication on an intraoperative user interface may be used to activate movement the robotic end effector to the planned alignment position.

The cut guide may be used as a guide for the surgical instrument to make a cut on the target object, such as to align the surgical instrument with a specific plane or line. By using a cut guide, a surgeon may retain control of the surgical instrument while also using the robotic arm to ensure that the surgical instrument is aligned with a predetermined cut plane or cut line. The robot in conjunction with a surgical navigation system allows for repeatable transfer of pre-defined surgical plan to the patient during the surgical procedure, while still allowing the surgeon some level of control over the final cuts.

The robotic arm may be tracked by a tracking system (which may include tracking the end effector or the cut guide). The tracking system may be used to determine a location of the cut guide, the end effector, the robotic arm, and the target object, among other things. The robotic arm may be controlled by a control system. The control system may move the robotic arm, such as in response to receiving a selection of the selectable indication on the user interface to move the robotic arm. The robotic arm may also be moved interactively by the surgeon through direct interaction with the end effector, or similar portions of the robotic arm.

A plurality of zones may be established around the target object using the tracking system, which maintains a virtual coordinate system around the surgical field. For example, a safety zone around the target object may be determined and maintained using the tracking system. The plurality of zones may include an interaction zone around the safety zone and a free-drive zone around the interaction zone. The free-drive zone may include an area of the surgical field or an area where the robotic arm is capable of moving, excluding other zones. The interaction zone may include a zone determined based on a selected location. For example, the selected location may include a location selected for the cut guide to move to in order to be within a cutting plane or cutting line or at a cutting position. The interaction zone may include an area surrounding the selected location (e.g., a few centimeters around the selected location, the selected location including an area capable of fitting the cut guide). The interaction zone may exclude a buffer zone, such as the safety zone. The safety zone may be a buffer zone immediately surrounding a portion of the target object. For example, in a total knee arthroplasty procedure, the safety zone may include a 20 centimeter sphere centered around a proximal end of a patient's femur. The safety zone may include a buffer zone around any portion of a patient. For example, the safety zone may continue (e.g., as a cone or funnel shape) away from the proximal end of the patient's femur up the remaining portion of the femur.

The robotic arm may be moved or restricted from movement in the zones according to various rules that may change based on a system state. The robotic arm may be moved autonomously (e.g., moved by the control system), moved interactively (e.g., by a surgeon), or both together (e.g., the surgeon may start an interactive movement, and the control system may control the robotic arm to make the interactive movement easier or have less resistance). Within certain zones, and in certain system states, the robot may restrict motion of the end effector in one or more directions or limit motion to a single direction or plane.

In an example, a first state may include a startup state before autonomous movement to align the cut guide with a cutting plane or line. In the first state, movement may be prevented within (or into) the safety zone. Movement may be allowed in the interaction zone and the free-drive zone when the system is in the first state. When the robotic arm is interactively moved into the interaction zone, an autonomous movement may be initiated. Upon initiation, the control system may move the robotic arm such that the cut guide is aligned in a cutting plane or line (as previously planned). This autonomous movement may trigger a change to a second system state. In the second system state, movement may be allowed only along the cutting plane or line. For example, interactive movement of the cut guide up or down along the line or along the plane may be permitted. Interactive movement may be prevented outside the line or plane. In the second state, movement may be permitted into the free-drive zone or the safety zone from the interaction zone (e.g., when the cut guide is moved along the cutting plane or line). Interactive movement in the second state may be restricted to movement along the cutting plane or line. For example, interactive movement may move the cut guide to a position adjacent to the target object within the safety zone along the cutting plane or line. The cut guide may be pinned to the target object, and a cut may be made by a cutting device using the cut guide.

After the cut guide is aligned in the cutting plane or line using the control system to move the robotic arm, the cut guide may be locked into place. Locking the cut guide may include restricting the cut guide to movement within the cut guide or plane. In an example, locking the cut guide may include locking the cut guide with respect to the target object. For example, if the target object is a target bone and the target bone moves, the cut guide may autonomously move to stay within the locked position, locked line, or locked plane, with respect to the target bone. The plurality of zones may move or change with movement of the target object as well. The target object may be tracked by the tracking system to determine changes to the target object location or orientation (e.g., tracked movement). In an example, locking the cut guide may include locking an orientation of the cut guide. The orientation (or position of the cut guide) may be defined within a coordinate system or with respect to the target object. In another example, a position or orientation of the target object may be determined by the tracking system within a coordinate system. In some examples, the coordinate system maintained by the tracking system is maintained relative to the target object, so if movement of the target object is detected the entire coordinate system shifts accordingly.

FIG. 1 illustrates a system 100 including a target object 102 and a plurality of zones in accordance with some embodiments. The plurality of zones may include a safety zone 104, an interaction zone 106, and a free-drive zone 108. The plurality of zones may be determined using a tracking system. For example, the tracking system may detect a position or an orientation of the target object 102 (e.g., a bone, a limb, a plurality of bones, a body part, etc.). From the position or the orientation of the target object 102, the tracking system may determine the plurality of zones. For example, the safety zone 104 may include a minimum distance (e.g., 10 cm, 20 cm, 40 cm, etc.) around the target object 102. The minimum distance may be determined based on surgical instruments to be used in surgery on the target object 102, applied forces or movement speed of objects in a surgical field, sensitivity or durability of the target object 102, power or control of a control system to control objects in a surgical field, or the like. The interaction zone 106 may include an area a radial distance away from the safety zone 104 (e.g., 5 cm, 10 cm, 30 cm, etc.). The free-drive zone 108 may include an area outside of the safety zone 104 or the interaction zone 106.

In an example, a control system may be used to control movement of a surgical instrument or robotic component in a surgical field of the system 100. In an example, the control system may allow interactive movement (e.g., controlled by a surgeon) and prevent autonomous movement (e.g., movement controlled by the control system) within the free-drive zone 108. In an example, the control system may allow interactive movement or autonomous movement within the interaction zone 106. In an example, the control system may prevent interactive movement or autonomous movement within the safety zone 104. In another example, the control system may allow movement of an object into the safety zone 104 under particular circumstances, as described below.

In an example, a robotic system may perform a commanded movement. For example, the robotic system may use sensors on an end effector or other area of the robotic arm to detect a manual manipulation of the robotic arm. The robotic arm may then command movement of the robotic arm according to the manual manipulation. For example, the commanded movement may include using a motor or control system driver to assist an interactive movement of the robotic arm. In another example, the robotic system may allow for back-driving or manual movement of the end effector.

The robotic system may perform a commanded movement of the end effector either as a defined displacement in its own coordinate system, or as a relative displacement with respect to the target object coordinate system. When the robotic system is interfaced with a tracking system (such as an optical tracking system), the coordinates of locations of interest may be relayed to the robotic system.

The robotic motion may also occur in response to an applied force on the end effector, such as when the robot has an integrated force-torque sensor. The MedTech ROSA robot, for example, has a force-torque sensor between the robot and the end effector. Thus, a force applied to the end effector (or the cut guide) may result in a corresponding commanded movement of the robotic arm. Other robots may have force-torque sensors in one or more joints, and may respond to an applied force anywhere on the robot arm.

FIGS. 2A-2D illustrate a surgical space 200A-200D including a robotic arm 204 and a target object 202 in accordance with some embodiments. The robotic arm 204 includes an end effector 206 and a cut guide 208 mounted to the end effector 206 of the robotic arm 204. The cut guide may be used to guide a surgical instrument, such as within a plane or a line. The surgical space 200A may include a plurality of zones, such as a safety zone 210, an interaction zone 212, and a free-drive zone 214.

Figure 2A:
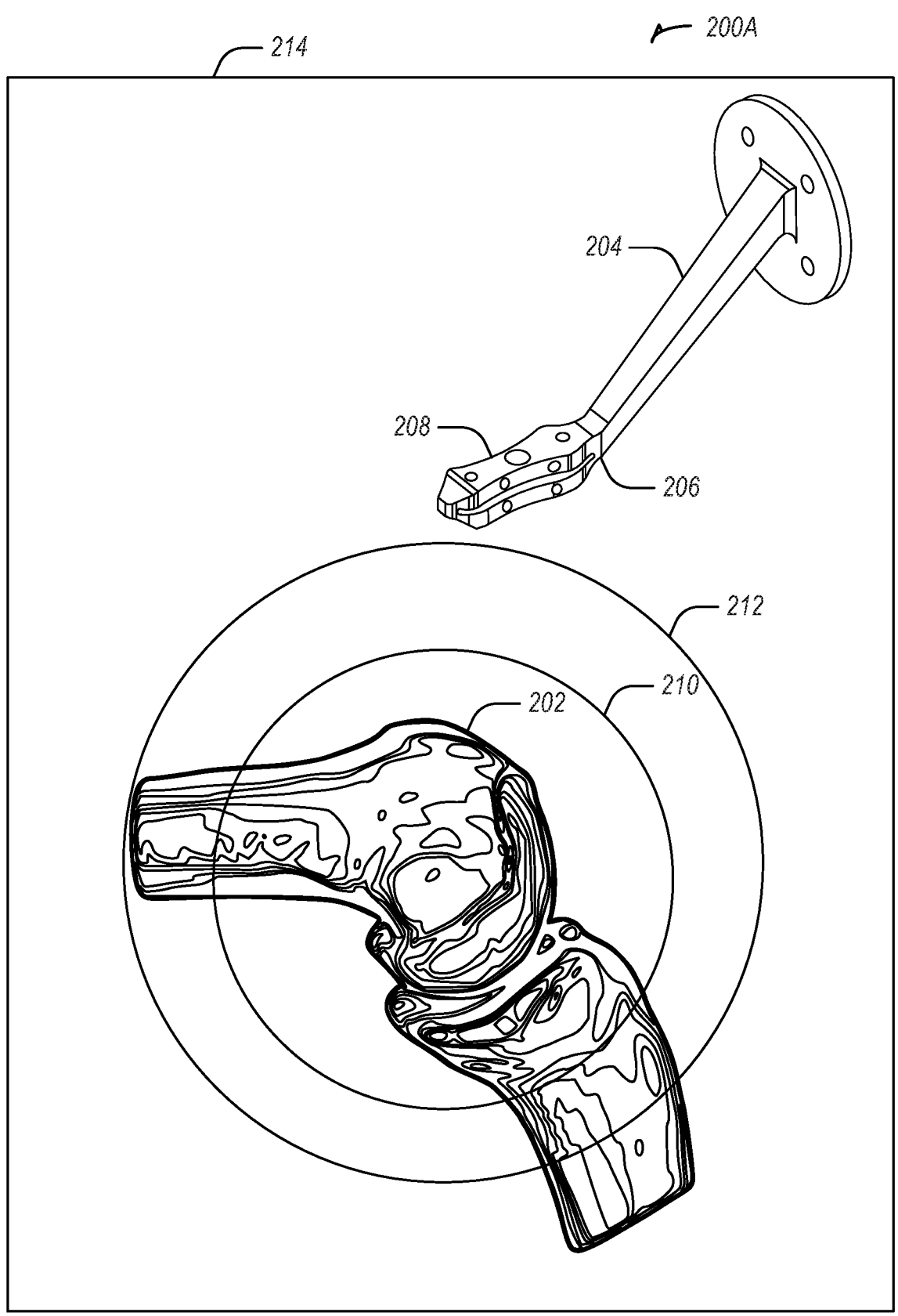
FIGS. 2A-2D illustrate a surgical space including a robotic arm and a target object in accordance with some embodiments.

FIG. 2A shows the surgical space 200A with the robotic arm 204, the end effector 206, and the cut guide 208 in respective first positions and first orientations. The surgical space 200A shows the end effector 206 and the cut guide 208 fully in the free-drive zone 214, and no part of the end effector 206, the cut guide 208, or the robotic arm 204 are in the interaction zone 212 or the safety zone 210. In an example, in the orientation shown in FIG. 2A, interactive movement of the robotic arm 204 may be permitted. For example, the robotic arm 204, the end effector 206, or the cut guide 208 may be moved by a surgeon or other person within the free-drive zone 214. A portion of the robotic arm 204 (e.g., including the end effector 206 or the cut guide 208) may be interactively moved into the interaction zone 212. Interactive movement into the safety zone 210 may be prevented (e.g., by a control system controlling the robotic arm 204).

The target object 202, the robotic arm 204, the end effector 206, or the cut guide 208 may be monitored by a tracking system to determine a position or an orientation of one or more of the components. The tracking system may establish the safety zone 210, the interaction zone 212, or the free-drive zone 214, in the sense that these zones are virtual geometries within a coordinate system maintained by the tracking system. The size and shape of the zones is predefined based on a particular procedure and instruments to be used in the procedure. The size and shape of the zones may change during the course of a procedure, such as if the instrument attached to the end effector of the robotic arm changes during the procedure. In an example, the free-drive zone 214 may include an area that the robotic arm 204 is capable of moving within excluding the interaction zone 212 and the safety zone 210. In another example, the free-drive zone 214 may include an area of the surgical space 200A excluding the safety zone 210 and the interaction zone 212 (e.g., excluding additional areas the robotic arm 204 may be configured to move, such as outside the surgical space 200A). The safety zone 210 may be established by the tracking system as an area surrounding the target object 202. The interaction zone 212 may be established by the tracking system as an area surrounding the safety zone 210. In an example, interactive movement of the cut guide 208 into the interaction zone 212 may initiate autonomous movement of the robotic arm 204 to position the cut guide 208 in a cutting position, such as aligned in an cutting plane or a cutting line. In an example, an autonomous movement may be prevented from moving the end effector 206, the cut guide 208, or the robotic arm 204 while all three are in the free-drive zone 214.

Figure 2B:
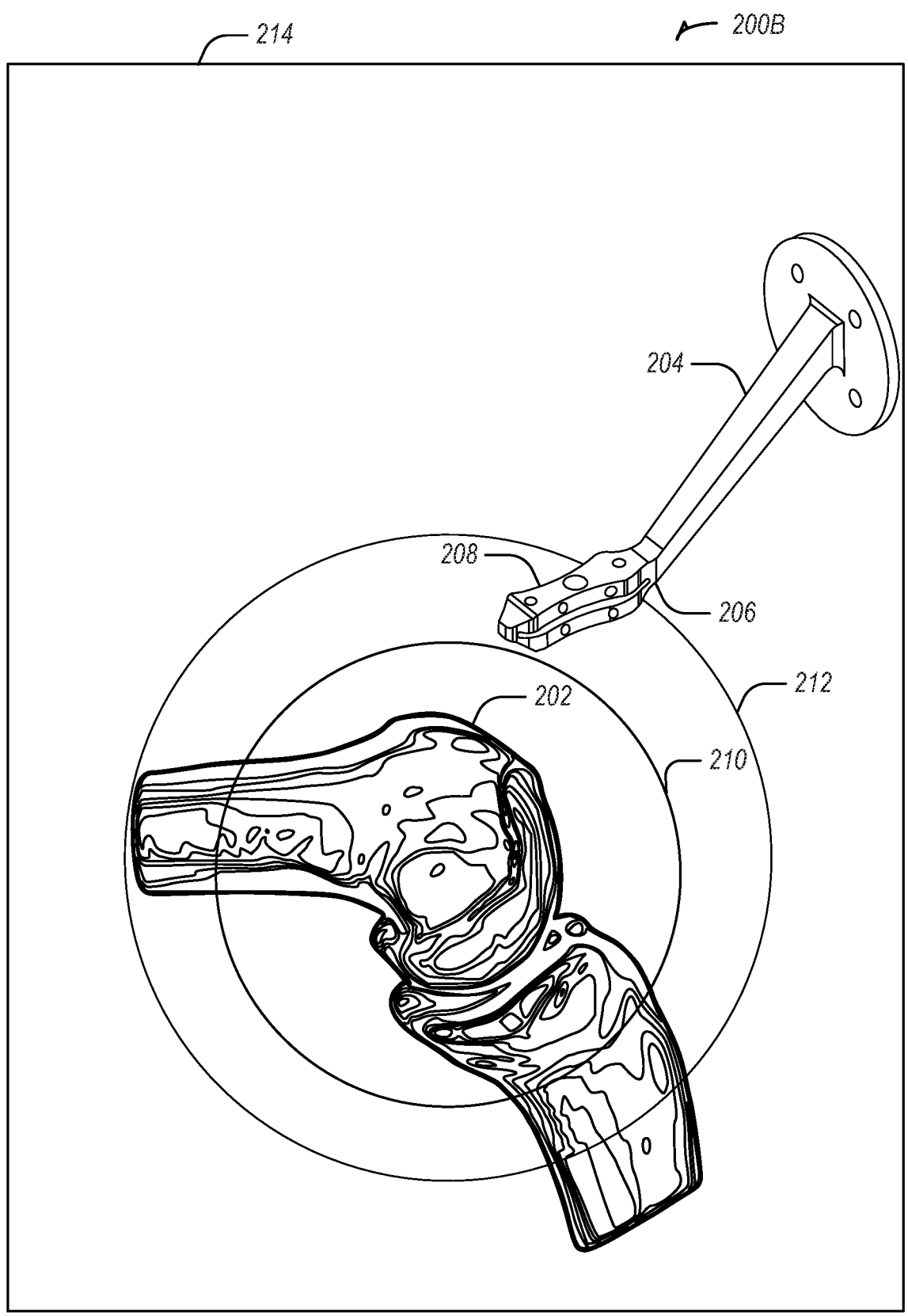

FIG. 2B shows the surgical space 200B with the robotic arm 204 moved from the first position displayed in the surgical space 200A to a second position. The robotic arm 204 in the second position remains in the free-drive zone 214. The surgical space 200B shows the end effector 206 and the cut guide 208 moved from the free-drive zone 214 (e.g., when at the first positions) to second positions within the interaction zone 212. In an example, when an interactive movement is attempted to move the end effector 206, the cut guide 208, or the robotic arm 204 into the safety zone 210, the interactive movement may be prevented. The movement of the robotic arm 204 from the first position in the surgical space 200A to the second position in the surgical space 200B may include an interactive movement.

After the cut guide 208 is positioned within the interaction zone 212, movement may be prevented or allowed depending on a system state. For example, in a first system state, interactive movement may be permitted within the interaction zone 212 and the free-drive zone 214. In the first system state, autonomous movement may be prevented. When an autonomous movement is activated (e.g., a selectable indication on a user interface is selected or an activation mechanism on the robotic arm 204 or elsewhere is activated), a control system may move the robotic arm 204 such that the cut guide is aligned in a cutting position, cutting line, or cutting plane. Selection or activation of the autonomous movement may change the system to a second system state, where autonomous movement is allowed and interactive movement may be prevented. After the cut guide 208 is moved autonomously, the system may enter a third system state where movement of the cut guide 208 is prevented outside of a locked position, a cutting line, or a cutting plane. In the third system state, autonomous movement may be allowed to keep the cut guide 208 in the aligned position (e.g., to keep the cut guide 208 aligned with the target object 202 if the target object 202 moves). In the third system state interactive movement may be allowed, such as within the cutting line or cutting plane. The cut guide 208 or the end effector 206 may be interactively moved into the safety zone 210 when the system in is in the third system state (e.g., after the cut guide 208 is autonomously moved to the cutting position, the cutting line, or the cutting plane).

Figure 2C:
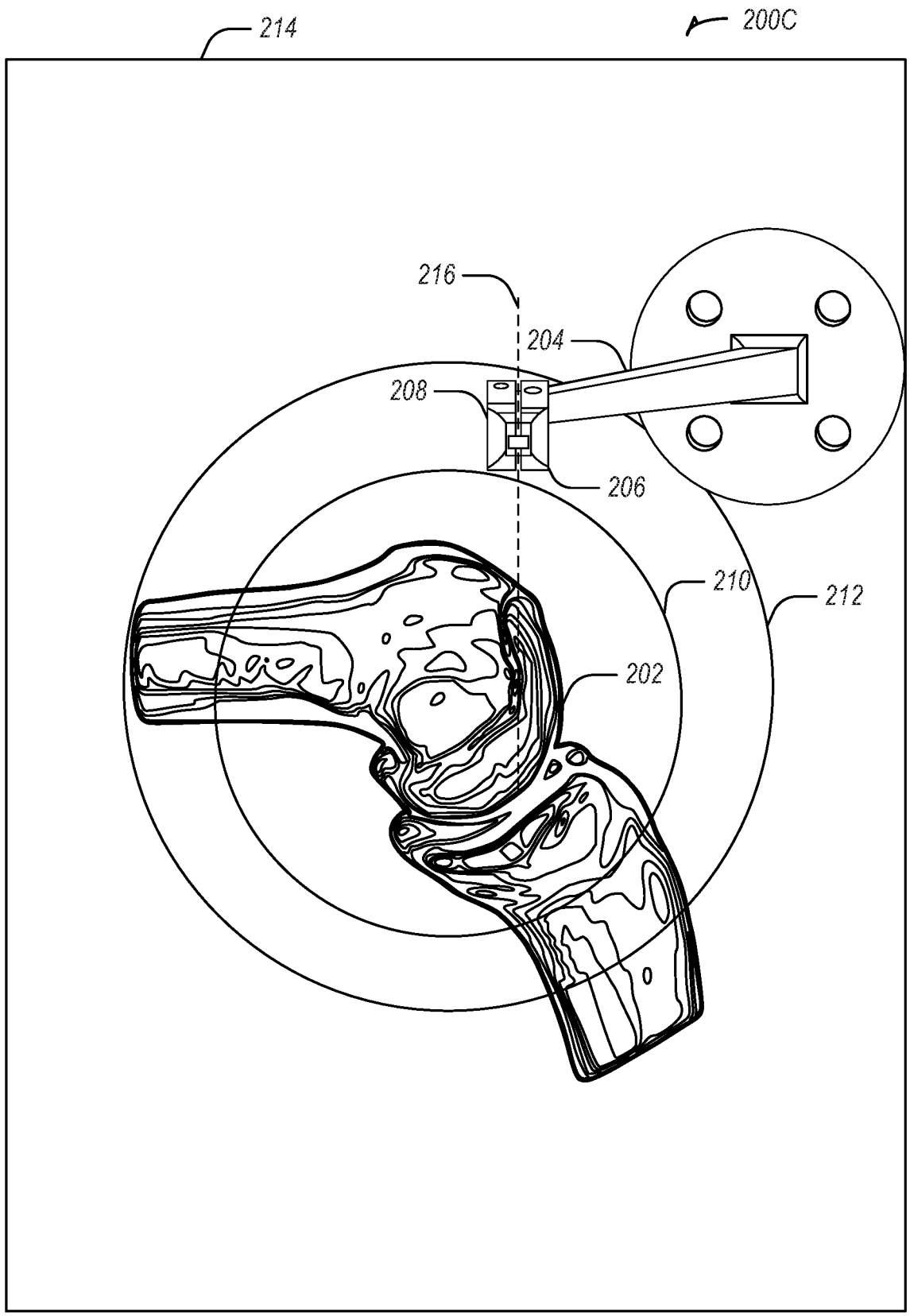

FIG. 2C shows the surgical space 200C with the robotic arm 204 partially in the free-drive zone 214 and partially in the interaction zone 212. The cut guide 208 and the end effector 206 are shown entirely in the interaction zone 212, although in an example, one or both may be partially in the interaction zone 212 and partially in the free-drive zone 214. The movement from the second position shown in the surgical space 200B of the end effector 206, the cut guide 208, or the robotic arm 204 to a third position shown in the surgical space 200C may include an autonomous movement. For example, a control system may drive the end effector 206, the cut guide 208, or the robotic arm 204 to the third position or orientation shown in the surgical space 200C. The autonomous movement may be initiated after the end effector 206, the cut guide 208, or the robotic arm 204 are placed in the interaction zone 212 (e.g., by an interactive movement from the free-drive zone 214). The initiation may include a selection on a user interface, a selection on a portion of the end effector 206, the cut guide 208, or the robotic arm 204, a voice command, or the like.

In an example, the surgical space 200C includes a cutting line or a cutting plane 216. The cut guide 208 may be aligned with the cutting line or cutting plane 216. For example, the autonomous movement from the second position shown in the surgical space 200B for the cut guide 208 to the third position shown in the surgical space 200C may move the cut guide 208 to a cutting position aligned with the cutting line or cutting plane 216.

Figure 2D:
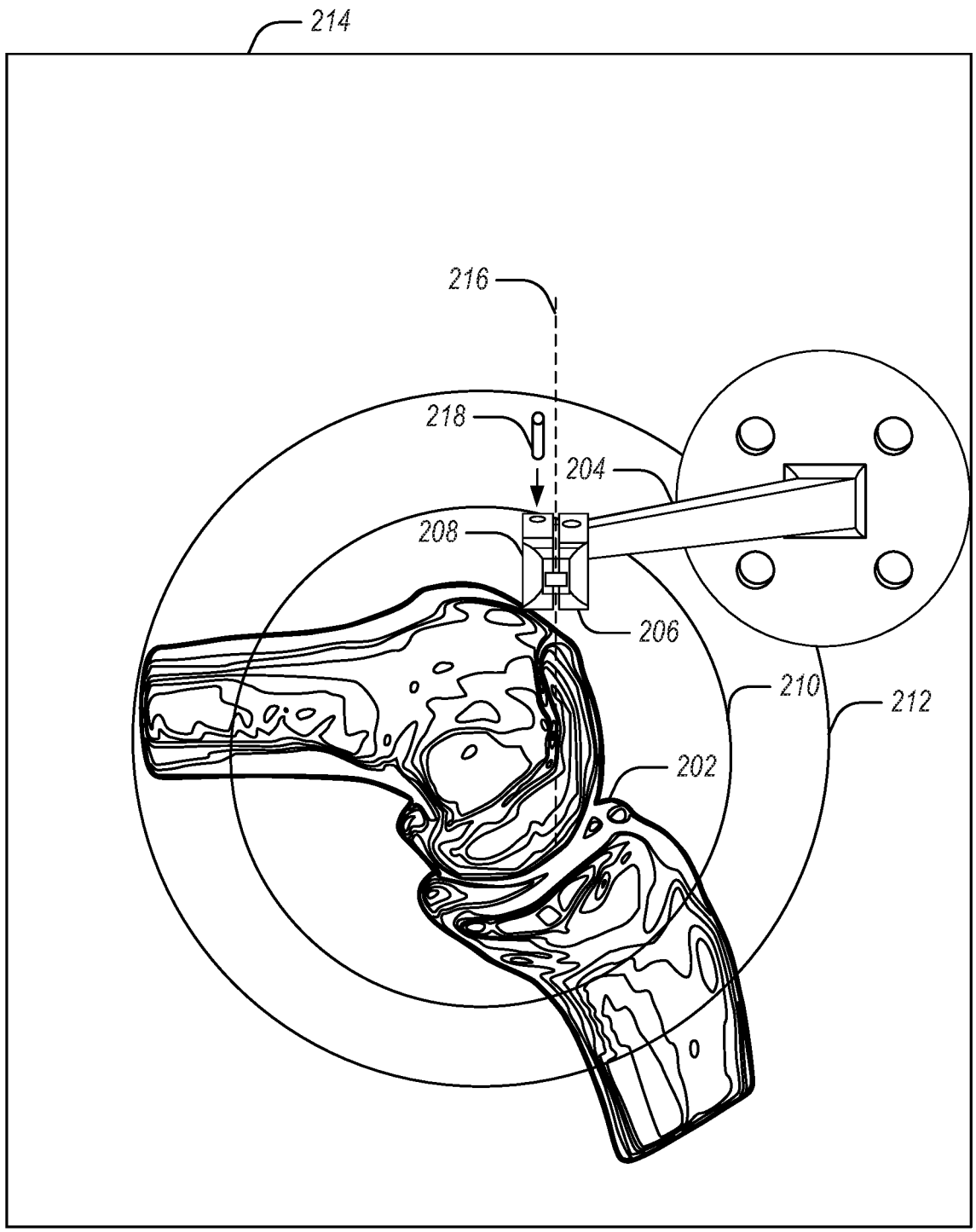

FIG. 2D shows the surgical space 200D with the cut guide 208 and the end effector 206, (and optionally the robotic arm 204) partially in the safety zone 210 and partially in the interaction zone 212. In an example, the robotic arm 204 may occupy all three zones. Movement of the cut guide 208 from the cutting position in the interaction zone 212 aligned with the cutting line or cutting plane 216 shown in the surgical space 200C to the cutting position in the safety zone 210 may be caused by an interactive movement. The cutting position in the safety zone 210 may be aligned with the cutting line or cutting plane 216. For example, in the surgical space 200C, the cut guide 208 may be locked to the cutting line or cutting plane 216. Locking the cut guide 208 may include locking the cut guide 208 to movement only along the cutting line or within the cutting plane 216. In an example, the cutting line or cutting plane 216 may be an absolute cutting line or plane within a coordinate system. In another example, the cutting line or cutting plane 216 may be a relative cutting line or plane, where the cutting line or plane is relative to a position or orientation of the target object 202. A position or orientation of the cut guide 208, for example, when in the cutting position or aligned with the cutting line or plane 216, may include a position or orientation relative to the position or orientation of the target object 202.

Movement of the cut guide 208 along the cutting line or plane 216 may include an interactive movement and an autonomous movement together. For example, if an interactive movement is initiated to move the cut guide 208 from the interaction zone 212 to the safety zone 210, the interactive movement may include a force that would cause the cut guide 208 to move out of the cutting line or plane 216. An autonomous movement (e.g., a force) may be generated by a control system to prevent the interactive movement from causing the cut guide 208 to leave the cutting line or plane 216.

The surgical space 200D may include a pin 218. The pin 218 may be used to secure the cut guide 208 to the target object 202. For example, the cut guide 208 may be secured before a cut is made on the target object 202. After the cut guide 208 is secured to the target object 202, the cut guide 208 may be controlled by a control system to move autonomously using the robotic arm 204 in response to movement of the target object 202. For example, in response to detecting slight movement of the target object 202 (e.g., using a tracking system), the control system may generate a small force to move the robotic arm 204 such that the cut guide 208 stays within the cutting line or plane 216 and in a fixed position relative to the target object. The pin 218 may be used to prevent movement (e.g., accidental interactive movement) of the cut guide 208 along the cutting line or plane 216. In another example, a selection may be made on a user interface to cause the cut guide 208 to be locked into a final position (e.g., in a coordinate system or relative to the target object 202). In response to the selection, the tracking system may monitor the target object 202 and the cut guide 208. If any movement of the target object 202 is detected, the control system may cause the robotic arm 204 to move the cut guide 208 to keep the cut guide 208 fixed with respect to the target object 202.

Figure 3:
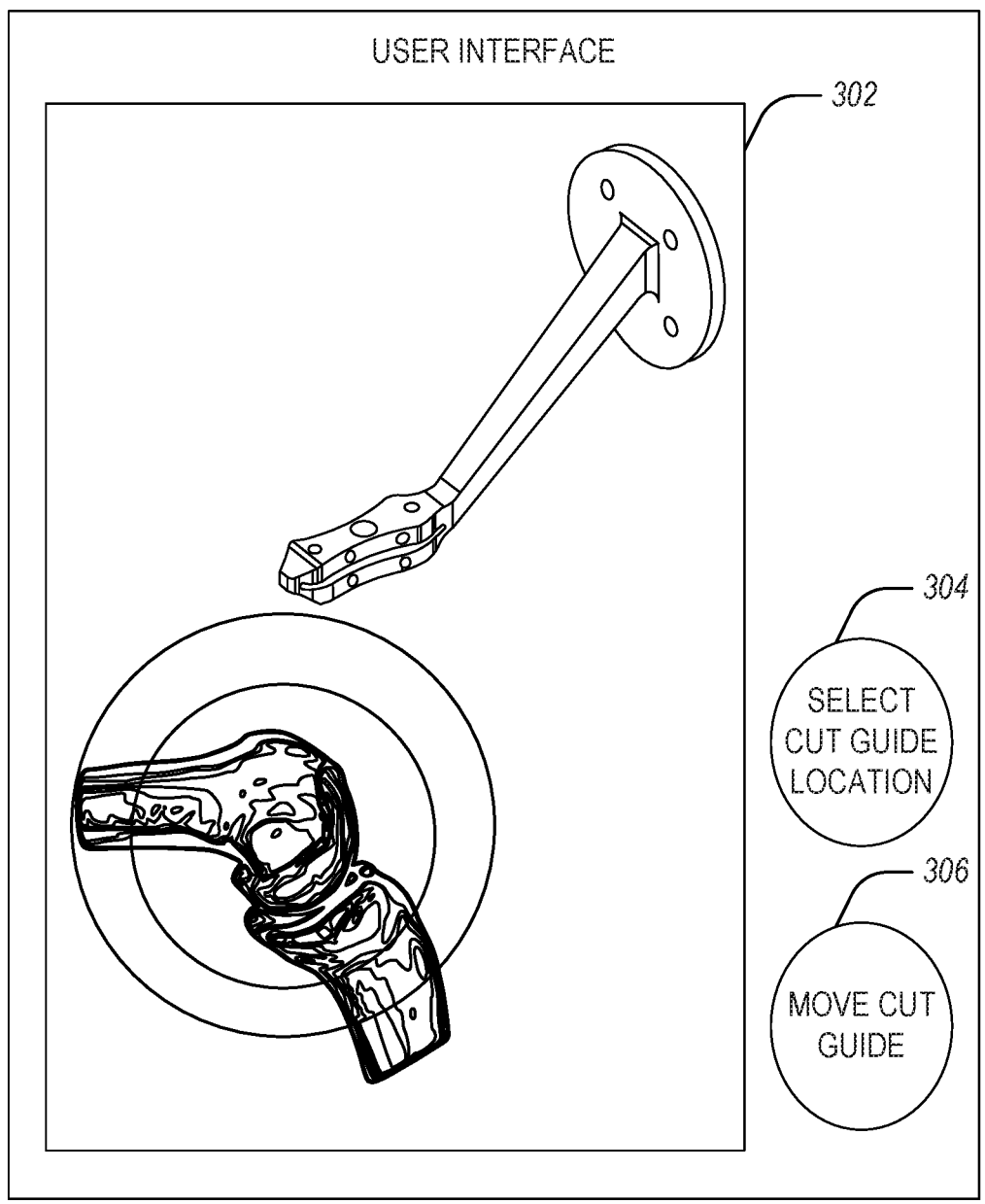
FIG. 3 illustrates a user interface for a tracking and control system in accordance with some embodiments.

FIG. 3 illustrates a user interface 300 for a tracking and control system in accordance with some embodiments. The user interface 300 may include a surgical space viewer 302, which may be virtual or a view from a camera. The surgical space viewer 302 may include a view of a target bone, one or more zones, and a robotic arm including an end effector including a cut guide. In an example, the surgical space viewer 302 may update a view in real-time.

The user interface 300 may include a cut guide location selection indication 304. The cut guide location selection indication 304 may be selected to predetermine a position or orientation for the cut guide. The surgical space viewer 302 may be used to select a locking position, cutting position, cutting line, or cutting plane for the cut guide after the cut guide location selection indication 304 is selected. For example, a user may drag the cut guide representation to a location. In an example, the user interface 300 may provide a recommended location, line or plane, for example based on previous selections. The surgical space viewer 302 may prevent selection of a location within a safety zone or within a free-drive zone. The surgical space viewer 302 may allow selection of a location within an interaction zone. For example, the surgical space viewer 302 may highlight or otherwise designate the interaction zone when the cut guide location selection indication 304 is selected.

The position of the cut guide may be determined by pre-operative or intraoperative planning techniques. Pre-operative planning techniques may use imaging (e.g., MRI, X-ray, CT, etc.) to graphically model the patient's bone. The pre-operative planning technique may be used (such as by the surgeon) to position a virtual implant on a bone model in the user interface 300 to visualize or assess implant position prior to performing cuts. The intraoperative technique may include using an optical system to register bone landmarks and graphically reconstruct the patient's bone. In an example, the intra-operative technique may be used in combination with pre-operative imaging. The intraoperative planning technique may be used to position a virtual implant on the bone model to visualize or assess planned cuts (e.g., using the user interface 300). When the surgeon is satisfied with the plan, the cut planes may be registered in the robotic system and the robotic arm may be prompted to position and orient the end effector to achieve planned cuts (e.g., align the end effector with a cut plane or cut line). The user interface 300 may be configured to be used for pre-operative planning, intraoperative planning, intraoperative real-time feedback, or post-operative evaluation. For example, different aspects of the user interface 300 may be used for planning and real-time feedback to allow the surgeon to plan and execute a procedure using the end effector and the robotic arm.

The user interface 300 may include a selectable indication 306, which upon selection, may cause a control system to move the cut guide. The cut guide may be moved by the robotic arm autonomously in response to the selectable indication 306 being selected. In an example, the selectable indication 306 may be unselectable when the cut guide is in the free-drive zone. In an example, the selectable indication 306 may be selectable only when the cut guide is in the interaction zone. In another example, the selectable indication 306 may be selectable regardless of zone, and the control system may autonomously move the cut guide only when the cut guide is first positioned within the interaction zone.

Figure 4:
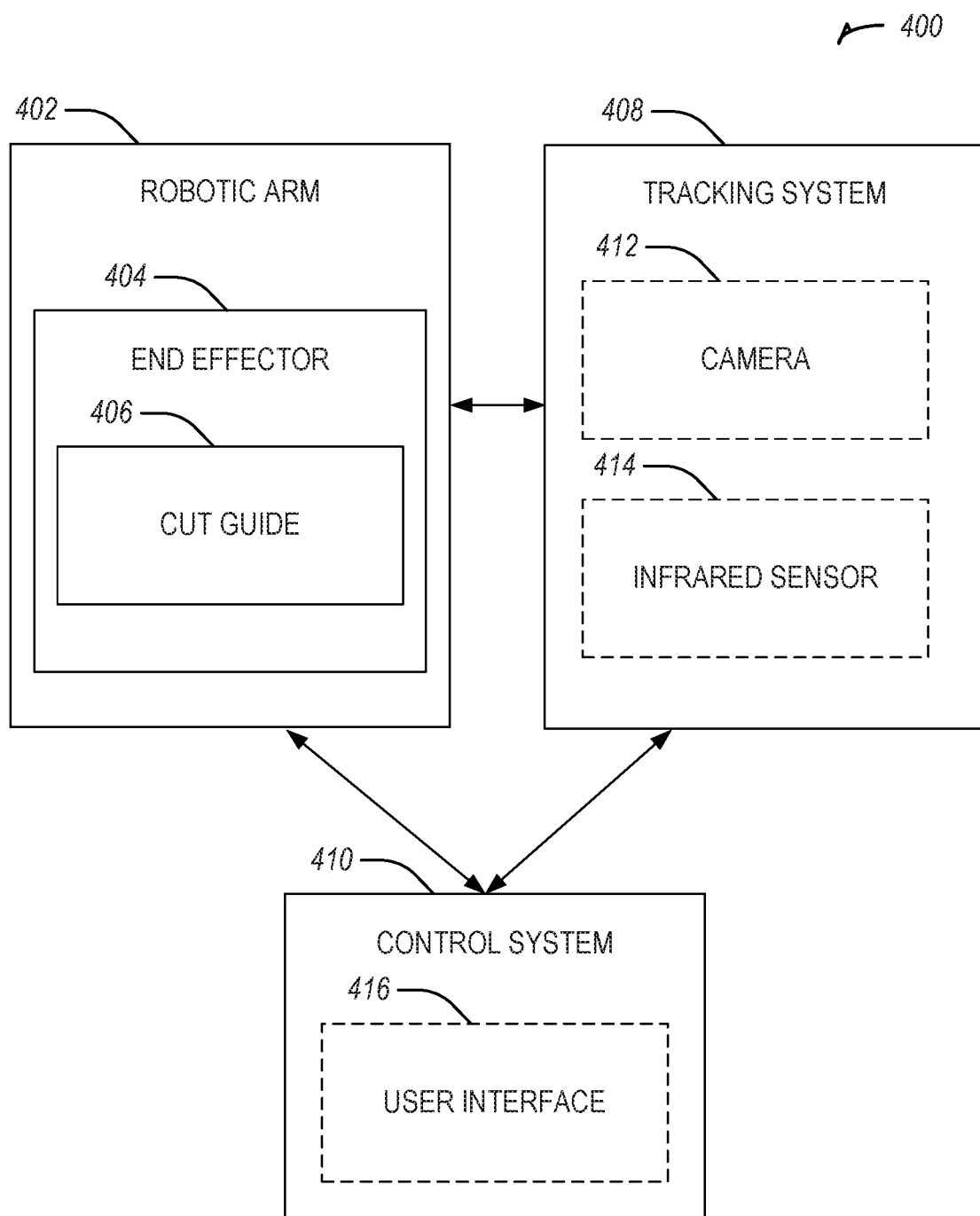
FIG. 4 illustrates a system for surgical tracking and control in accordance with some embodiments.

FIG. 4 illustrates a system 400 for surgical tracking and control in accordance with some embodiments. The system 400 may include a robotic arm 402, a tracking system 408, and a control system 410.

The robotic arm 402 may include an end effector 404, including a cut guide 406 mounted on the end effector 404. The robotic arm 402 may be configured to allow interactive movement and controlled autonomous movement of the end effector 404. The cut guide 406 may be configured to guide a surgical instrument within a line or plane (e.g., a cutting device to cut a target object).

The tracking system 408 may optionally include a camera 412 or an infrared sensor 414. The tracking system 408 may use the camera 412 or the infrared sensor 414 to track the robotic arm 402, the end effector 404, the cut guide 406, a target object, or the like. In an example, the tracking system 408 may be used to determine a position or an orientation of the cut guide 406. The position or the orientation may be determined relative to a coordinate system or relative to a target object. An example optical tracking device commonly used for this type of application is the Polaris Optical Tracking System from Northern Digital of Waterloo, Ontario, Canada.

The control system 410 may optionally include a user interface 416. In another example, the user interface 416 may be separate from the control system 410 or may be communicatively coupled to the control system 410. The control system 410 may be used to determine a zone occupied by the cut guide 406, such as using the position or the orientation of the cut guide, a target object, or a coordinate system. The zone may include a safety zone, an interaction zone, or a free-drive zone. In response to determining the zone is a free-drive zone, the control system 410 may permit interactive movement of the end effector 404 and prevent autonomous movement of the end effector 404. In response to determining the zone is an interactive zone, the control system 410 may permit interactive movement and autonomous movement of the end effector 404.

The control system 410 may prevent movement (autonomous or interactive) into the safety zone. In an example, the control system 410 may, in response to determining that the zone is the interaction zone, cause autonomous movement of the end effector 404 to a cutting position. The autonomous movement may be caused in response to selection of a selectable indication for the movement on the user interface 416. The user interface 416 may be used to select a predetermined cutting position, such as a position relative to the target object. In an example, the control system 410 may disable the selectable indication in response to determining the zone is a free-drive zone. In an example, the control system 410 may activate the selectable indication in response to determining that the zone is the interaction zone.

After moving the end effector 404 to the cutting position, the cut guide 406 may be allowed to move interactively along a cut plane or cut line. The cut guide 406 may be prevented from moving outside of the cut plane or cut line by the control system 410. In an example, the cut guide 406 may be permitted to enter the safety zone by the control system 410 while the cut guide 406 is in the cut plane or cut line. This permission may occur, in an example, only after autonomous movement of the cut guide 406 to the cutting position.

In an example, the control system 410 may lock the cut guide 406 into the cutting position after causing the cut guide 406 to move to the cutting position. Locking the cut guide 406 may include locking a position or an orientation of the cut guide 406, locking the cut guide to a cut plane or a cut line, locking the cut guide with respect to a coordinate system, or locking the cut guide with respect to a target object (e.g., a position, distance, or orientation of the target object).

In an example, the tracking system 408 may determine a trajectory of the cut guide 406, such as from an interactive force applied to the cut guide 406, the end effector 404, or the robotic arm 402. The control system 410 may determine that the trajectory would cause the robotic arm 402 or a portion of the robotic arm, the end effector 404, or the cut guide 406 to enter the safety zone. In response to determining that the trajectory would cause entry into the safety zone, the control system 410 may prevent movement of the robotic arm 402.

In an example, the control system 410 may establish the interaction zone using anatomical landmarks of the target object (e.g., a target bone) or identified locations of the target object (e.g., digitized locations). The tracking system 408 may determine a position or an orientation of a target object relative to the coordinate system. The position or the orientation of the cut guide 406 may be determined relative to the position or the orientation of the target object by the tracking system. In an example, the coordinate system is determined from the position or the orientation of the target object.

Figure 5:
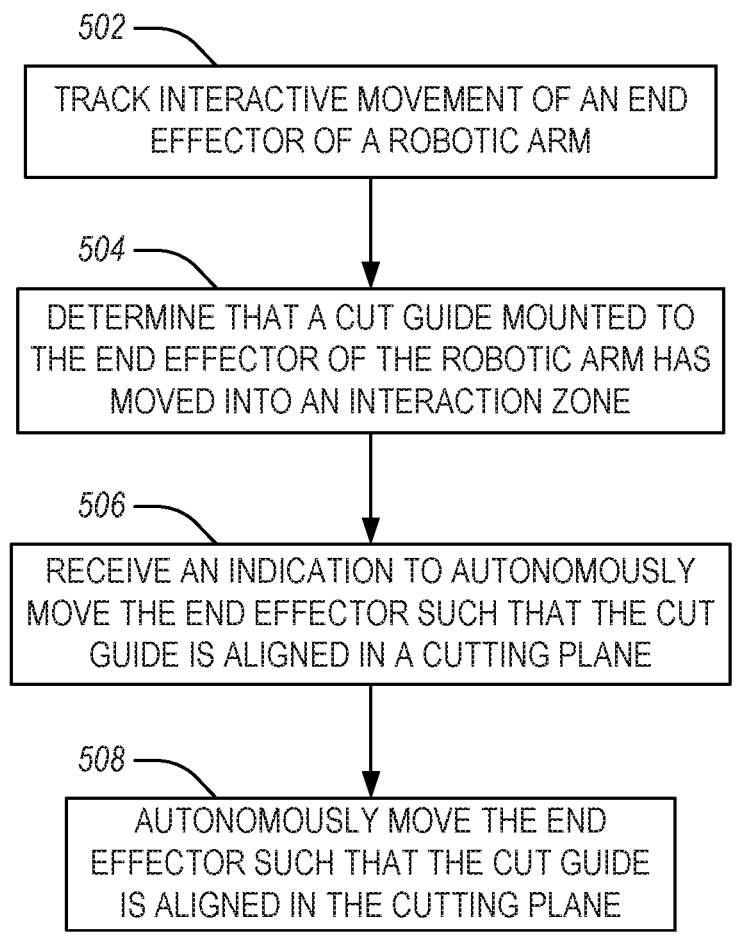
FIG. 5 illustrates a flow chart showing a technique for surgical tracking and control in accordance with some embodiments.

FIG. 5 illustrates a flow chart showing a technique 500 for surgical tracking and control in accordance with some embodiments. The technique 500 includes an operation 502 to track interactive movement of an end effector of a robotic arm. The interactive movement may be tracked using a tracking system. The technique 500 includes an operation 504 to determine that a cut guide mounted to the end effector of the robotic arm has moved into an interaction zone. The cut guide may be moved from a free-drive zone to the interaction zone. The interaction zone may include an area around a target object, such as a portion of a sphere around the target object. The interaction zone may exclude an area immediately surrounding the target object, such as a safety zone.

The technique 500 includes an operation 506 to receive an indication to autonomously move the end effector such that the cut guide is aligned in a cutting plane. The technique 500 includes an operation 508 to autonomously move the end effector such that the cut guide is aligned in the cutting plane. The technique 500 may include locking the cut guide into the cutting plane. Locking the cut guide may include locking the cut guide with respect to a coordinate system or a target object. For example, the cut guide may be locked into the cutting plane with respect to the target object such that when the target object moves, a control system causes the cut guide to autonomously move with the target object.

The technique 500 may include an operation to determine, such as using the tracking system, a trajectory of the cut guide, such as from an interactive force. The technique 500 may include determining that the trajectory would cause the robotic arm to enter a safety zone. The safety zone may be between the interaction zone and the target object. In response to determining that the trajectory would cause the robotic arm to enter the safety zone, the technique 500 may include preventing movement of the robotic arm into the safety zone. Preventing the movement may include counteracting the interactive force with an autonomous force from a control system.

The technique 500 may include presenting a user interface, including a selectable indication. The technique 500 may include receiving an input directed to the selectable indication. In response to the input, the cut guide may be autonomously moved to the cutting position, such as by a control system. In an example, the technique 500 includes disabling the selectable indication in response to determining that the cut guide is in a free-drive zone or activating the selectable indication in response to determining the cut guide is in the interaction zone.

Figure 6A:
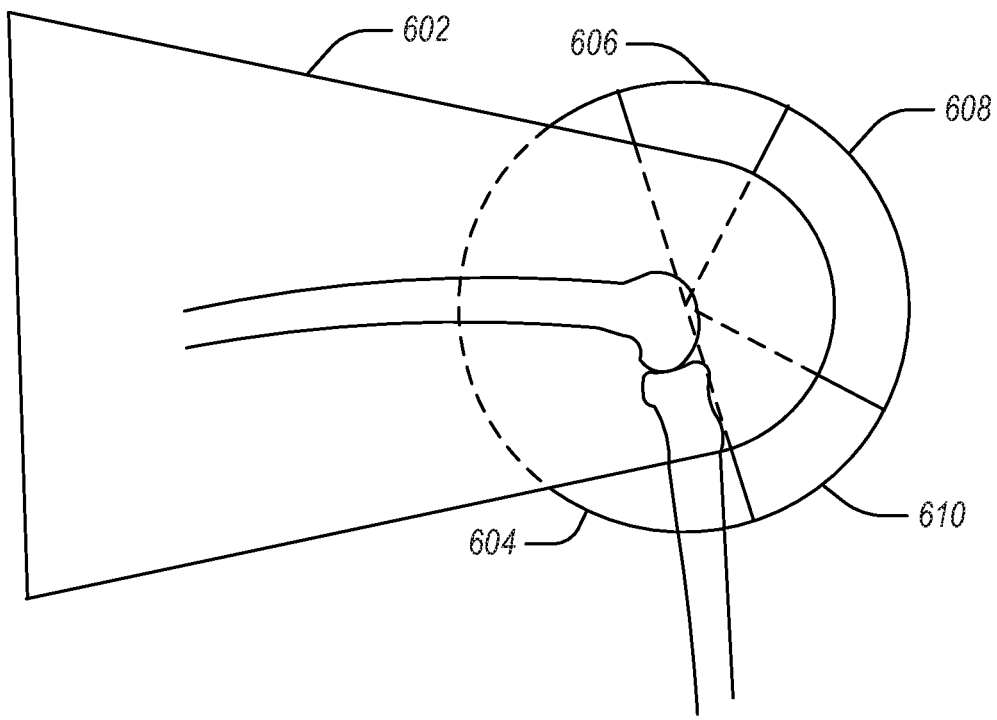
FIG. 6A illustrates a system showing system state zones in accordance with some embodiments.

FIG. 6A illustrates a system 600A showing system state zones in accordance with some embodiments. The system 600A includes a safety zone 602 and an interaction zone 604. The interaction zone 604 may include subzones, such as specific cutting subzones, specific sawing subzones, specific burring subzones, subzones specific to surgical procedures (e.g., a total knee arthroplasty, a hip replacement, etc.), or the like. The subzones may be preset for a particular procedure. The subzones may be used for navigating within the interaction zone 604 to initiate a particular procedure. For example, a surgeon may place an end effector into a first subzone to initiate a first procedure, and then move the end effector (e.g., after the procedure has occurred) to a second subzone to initiate a second procedure. The first procedure may include an autonomous movement (e.g., to a cutting plane or other alignment plane), performance of a cut or surgical procedure, and may include engaging or disengaging the end effector from a target object. After the first procedure is complete, the end effector may be moved to a second subzone for performance of a second procedure. For example, a total knee arthroplasty often requires multiple cuts in two or more different planes. The end effector may be moved to a first subzone for performing a first cut (e.g., after autonomously moving the end effector to align a cut guide in a first cutting plane), and then moved to a second subzone for performing a second cut.

The system 600A illustrates, as an example, three specific subzones related to a total knee arthroplasty. One or more of these subzones may be used in a total knee arthroplasty. For example, a femur-specific interaction zone 606, a 4-in-1-specific interaction zone 608, and a tibia-specific interaction zone 610 are shown in FIG. 6A. Zones for cutting, burring, or sawing of other joints or body parts may include respective bone-specific or location-specific zones, and the subzones are not limited to the three illustrated in FIG. 6A. The specific interaction zones (e.g., 606-610) may be subzones of the interaction zone, such as for purposes of placing an end effector into the subzones. The subzones may extend into the safety zone, such as for guiding an end effector after the end effector is locked into a plane or line for cutting, burring, or sawing. The 4-in-1-specific interaction zone 608 may be used with a 4-in-1 cut guide, such as those manufactured by Zimmer Biomet of Warsaw, Ind. The 4-in-1 cut guide may be used in a total knee arthroplasty for making finishing cuts. In an example, other finishing cut guides may be used in the 4-in-1-specific interaction zone 608, which is named herein for convenience and illustration, but may include other cut guides.

In an example, manually moving an end effector into certain zones may trigger different system surgical states. For example, when the end effector is brought into the femur-specific interaction zone 606, the system may enter a femur resection state. Entering the femur resection state may cause a user interface to show a femur resection plan. When the femur resection plan is selected by the user (e.g., a surgeon), the end effector may be moved to align with a cut line or cut plane related to the femur resection. In an example, when the end effector is brought into the tibia-specific interaction zone 610, the system may enter a tibia resection state, which may cause the user interface to show a tibia cutting plan. The tibia cutting plan may be selected by the user on the user interface, for example, to move the end effector automatically to a tibia cutting plane or line. In an example, when the end effector is brought into the 4-in-1-specific interaction zone 608, the system may enter a 4-in-1 resection state, which may cause the user interface to show a 4-in-1 cutting plan. The 4-in-1 cutting plan may be selected by the user to move the end effector to a 4-in-1 cut plane or line.

Other interaction zones may be preselected for performing surgical techniques. For example, a location for another surgical procedure (e.g., for sawing) may be designated as a sawing interaction zone. The sawing interaction zone may operate similarly to the other specific interaction zones 606-610 described above. For example, the sawing interaction zone may be a subzone of the interaction zone or the sawing interaction zone may be subject to a safety zone (e.g., where autonomous or interactive movement of the end effector is prevented until after the end effector is autonomously moved into a sawing plane or line).

The surgical states (e.g., femur, tibia, 4-in-1) corresponding to the specific interaction zones (e.g., 606-610) may be automatically controlled by the position of the end effector. For example, the system 600A may automatically enter the femur surgical state when the end effector is moved (e.g., interactively or via a commanded movement) into the femur-specific interaction zone 606. Changing to a surgical state (e.g., from a free-drive zone or from another surgical state) may cause a user interface to display a selection to move an end effector to a predetermined plane or line corresponding to a surgical action associated with the surgical state.

Figure 6B:
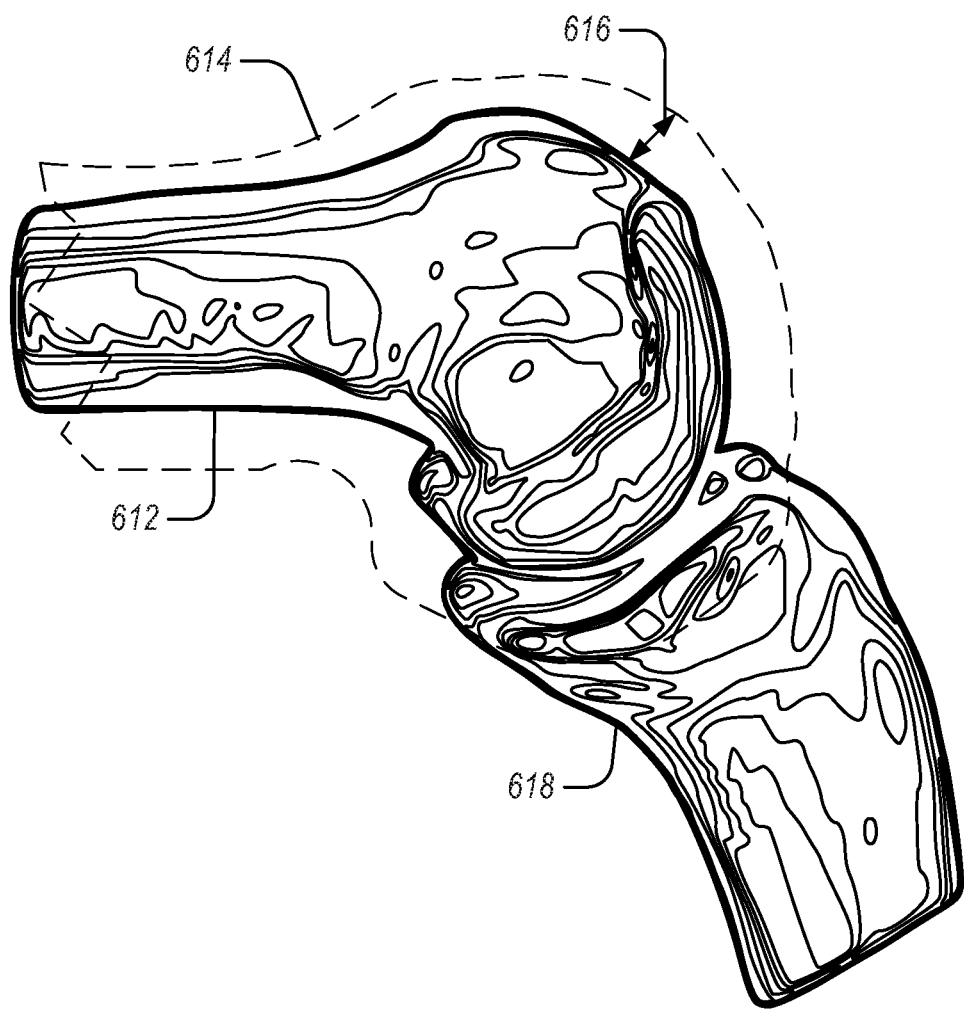
FIG. 6B illustrates a safe zone around a femur and tibia for use with a robotic arm in accordance with some embodiments.

FIG. 6B illustrates a safe zone 614 around a femur 612 and tibia 618 for use with a robotic arm in accordance with some embodiments. The safe zone 614 may include a predetermined distance 616 around the femur, such as 5 centimeters from the bone (e.g., radially outward from an outside portion of the bone). In an example, the safe zone 614 may intersect with the tibia 618. In another example, the safe zone 614 may extend around the tibia 618 as well. In yet another example, the safe zone 614 may go around the tibia 618 and intersect with the femur 612. The predetermined distance 616 may be a uniform distance around the femur 612, or may increase or decrease with distance from, for example, a distal end of the femur 612.

The safe zone 614 may be used as an area where only autonomous movement of a robotic arm is allowed, which may include resisting interactive movement (e.g., preventing a surgeon from moving the robotic arm by countering a force imparted by the surgeon). Alternatively, within the safe zone 614 the robot may be programmed to ignore interactive input from the surgeon and only respond to commanded (autonomous) movements. The autonomous movement may include movement only within a plane or axis (e.g., a cutting plane or axis) where the robotic arm may have been moved into the plane or axis within an interaction zone or some other zone before the robotic arm autonomously moves into the safety zone 614. In an example, the safety zone 614 may be used to prevent or allow a particular speed for a robotic arm operating within the safety zone 614. For example, the speed of the robotic arm may be limited when within the safety zone 614 to a medium or slow speed compared to a fast or unlimited (e.g., subject to the power of the motors controlling the robot) speed when in other zones (e.g., a free drive zone or an interaction zone). In some examples, the robot may be programmed with increased sensitivity within the safety zone 614, where the increased sensitivity includes detecting forces on the end effector. In these examples, if the end effector comes into contact with the patient or an instrument within the safety zone it may be immediately detected and the movement stopped or reversed. Increased sensitivity may be optionally configured and set to different force input settings.

In an example, a robotic arm may be controlled by a controlling device such as a pedal, handheld device, or a user interface of a robotic controller. When the controlling device is activated, the robotic arm may enter the safety zone 614, exit the safety zone 614, lock into a plane or axis, or the like. In an example, when the controlling device is released, the surgeon operating the controlling device may be asked to reactivate the controlling device when the robotic arm (or a cut guide or end effector of the robotic arm) is outside the safety zone 614. When a portion of the robotic arm, such as a cut guide or end effector is within the safety zone 614, the surgeon may be asked whether the cut guide is pinned. When pinned, the robotic arm may be prevented from moving.

When the cut guide is not pinned, the robotic controller may restart bone tracking or robotic arm movement (e.g., exit the safety zone 614).

Figure 7A:
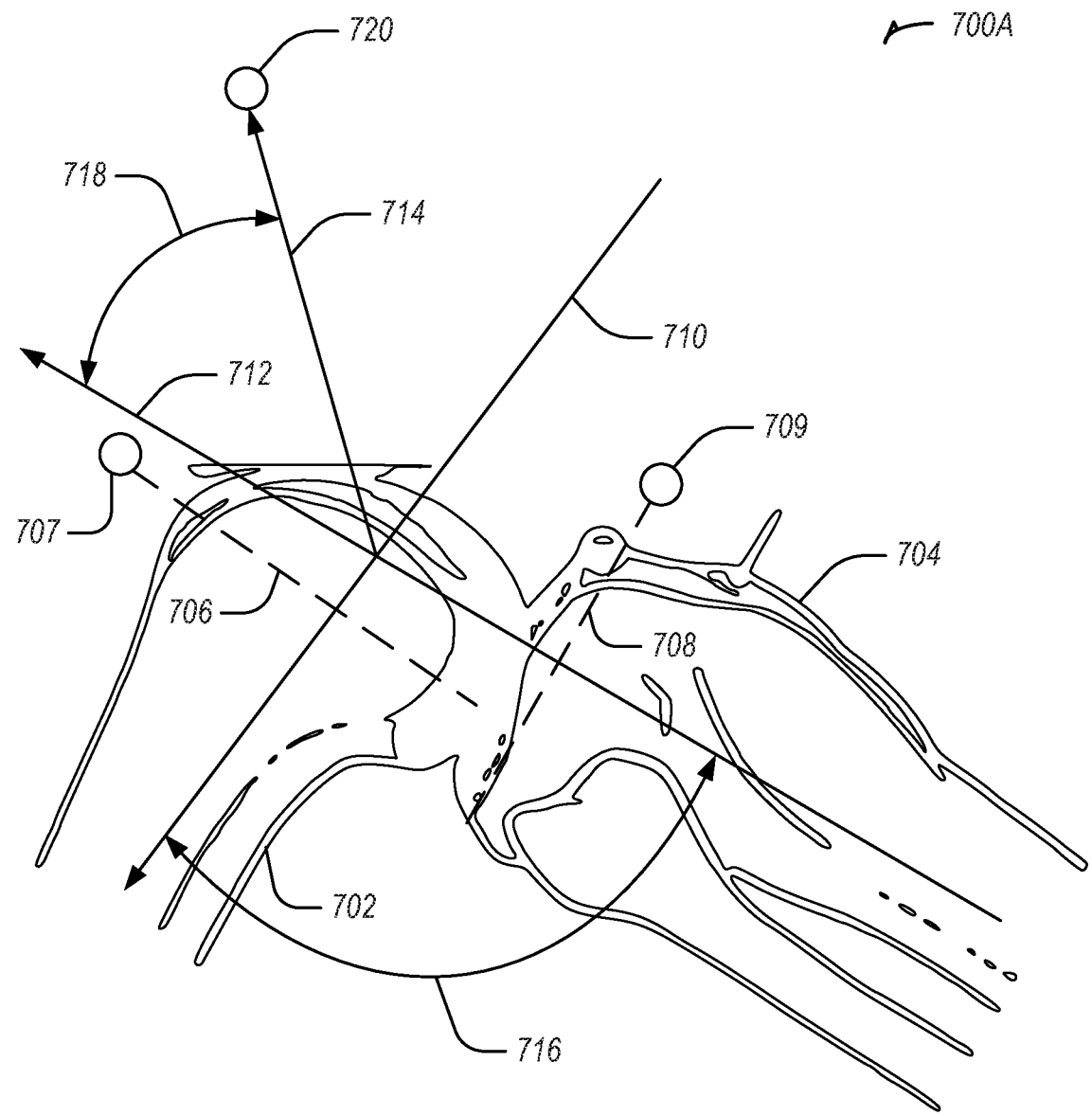
FIGS. 7A-7C illustrate three examples of a safe position for an end effector of a robotic arm within a femoral sagittal plane in accordance with some embodiments.
Figure 7B:
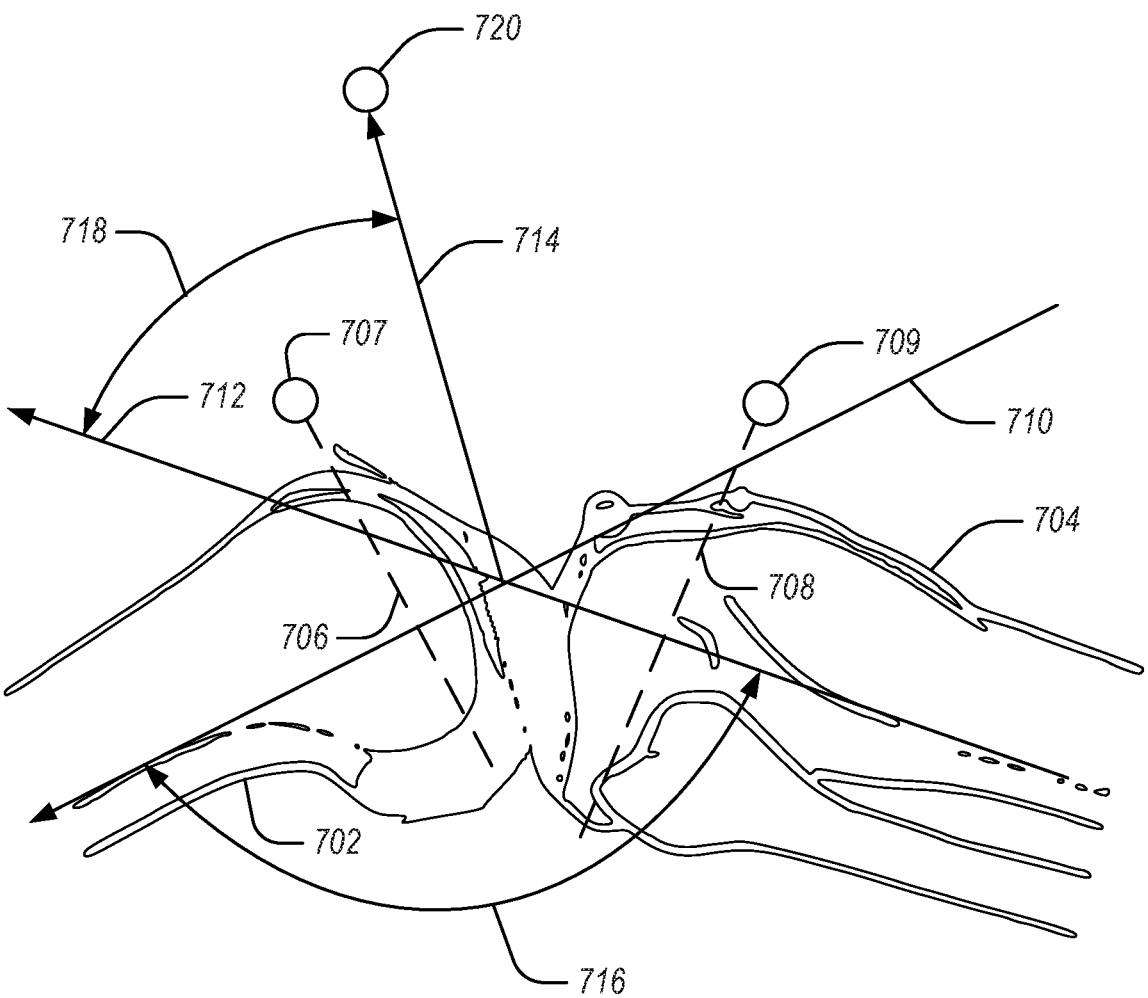
Figure 7C:
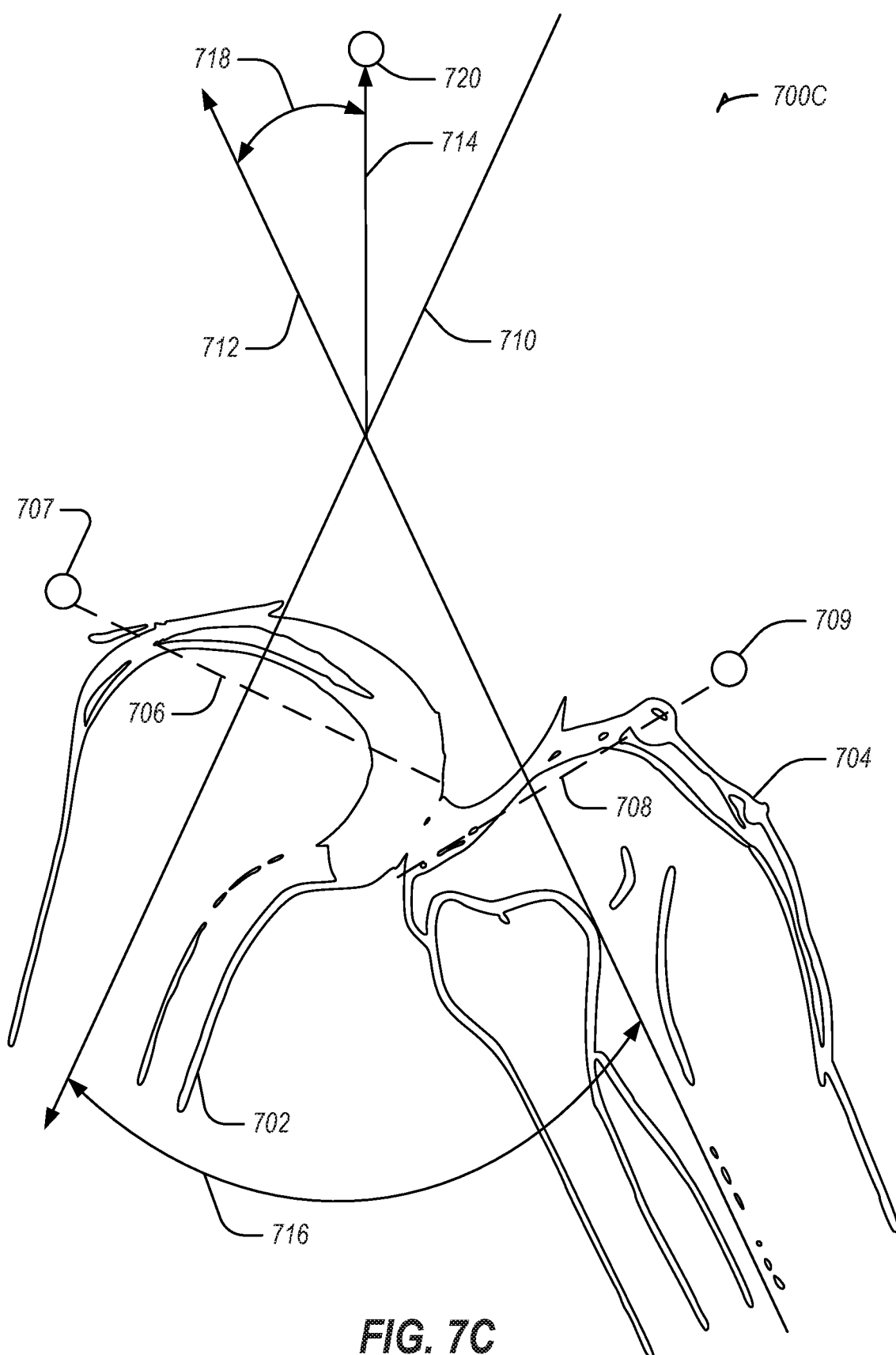

FIGS. 7A-7C illustrate three examples 700A-700C of a safe position for an end effector of a robotic arm within a femoral sagittal plane in accordance with some embodiments. FIG. 7B illustrates a femur 702 and a tibia 704 in a substantially extended leg position, FIG. 7C illustrates the femur 702 and the tibia 704 in a substantially bent position, and FIG. 7A illustrates the femur 702 and the tibia 704 in a partially bent position.

In an example, the femur 702 and the tibia 704 may be used to determine reference lines including for example, a femoral mechanical-anatomical (FMA) axis 710 or a tibial mechanical-anatomical (TMA) axis 712. In an example, a cutting line or plane may be used to determine a position to perform a cut, such as in a total or partial knee arthroplasty. For example, a distal cut line or plane 706 may be used as a cut line or plane for cutting the femur 706. A distal cut plane position 707 may be defined as a position for a robotic arm to begin to perform a femoral cut on the femur 702. A proximal cut line or plane 708 may be used as a cut line or plane for cutting the tibia 704, with a proximal cut plane position 709 defining a position for the robotic arm to begin to perform a tibial cut on the tibia 704. In an example, the distal cut plane position 707 may represent a first position for a femoral cut and the proximal cut plane position 709 may represent a second position for a tibial cut. A cut guide, such as a two slot cut guide (e.g., as shown below in FIGS. 8A-8C) affixed to a robotic arm may transition between the first and second positions, as controlled by the robotic arm. When the cut guide is the two slot cut guide, the robotic arm may translate the cut guide from the first position to the second position (or vice versa) without rotation or with minimal rotation, which may save time during the procedure.

The examples 700A-700C illustrate a safety vector 714, at the end of which is a safe position 720. The safe position 720 is selected to avoid contact between the cut guide, end effector, or instrument and a patient or other instruments (e.g., retractors, bone references, etc). The safety vector 714 may be offset from the TMA axis 712 at an angle 718 equal to theta divided by 'y.' The value 'y' may be predetermined such that the safety vector 714 or the safe position 720 is adequately offset from the TMA axis 712 or the FMA axis 710. For example, 'y' may be set to equal 2 such that the safety vector 714 is halfway from the FMA axis 710 to the TMA axis 712 (i.e., the safety vector 714 bisects the angle between the FMA axis 710 and the TAM axis 712). In an example, the value of 'y' may be set to other values, such as 4 or ½ such that the safety vector is closer or further from one of the FMA axis 710 or the TMA axis 712, which may be used in a procedure where additional safety is desired away from one of the axes 710 or 712. In an example, the safety vector 714 may be offset at an angle from the FMA axis 710. An angle theta 716 may correspond to the bending angle of the joint of the knee formed by the angle between the FMA axis 710 and the TMA axis 712. The angle theta 716 divided by a value 'y' is then used to determine the angel 718, used to offset the safety vector 714 from the TMA axis 712, away from the femur 702. The safety vector 714 may have a predetermined distance (e.g., 20 cm), from an intersection of the FMA axis 710 and the TMA axis 712. At the end of the safety vector 714, a safety position 720 for the robotic arm may be defined. In an example, a portion of the robotic arm may transition among the safety position 720, the distal cut plane position 707, and the proximal cut plane position 709. For example, a cut guide affixed to an end of the robotic arm may be positioned by the robotic arm (automatically or interactively) at the safety position 720. A procedure may be initiated, and the robotic arm may transition the cut guide from the safety position 720 to the distal cut plane position 707 to perform a femoral resection. After the femoral resection is completed, the robotic arm may autonomously move the cut guide to the proximal cut plane position 709, and a tibial resection may be performed. After the tibial resection is completed, the robotic arm may return the cut guide to the safety position 720. In another example, the tibial resection may occur before the femoral resection. In yet another example, the cut guide may optionally be commanded to return to the safe position 702 between cuts.

In an example, when a procedure is initiated, the robotic arm may automatically move a cut guide, end effector, or instrument to the safe position 720, which is determined based on the femur and tibia position (e.g., angle between their mechanical axes) as described above. After the safe position 720 is reached, the cut guide, end effector, or instrument may be moved (autonomously or interactively) to the final cutting position (e.g., the distal cut plane position 707 or the proximal cut plane position 709). When the robotic arm moves the cut guide, end effector, or instrument interactively, the robotic arm may determine a plane or axis to approach the distal cut plane position 707 or the proximal cut plane position 709 from the safe position 720, and the speed of the robotic arm may be controlled by a surgeon.

Figure 8A:
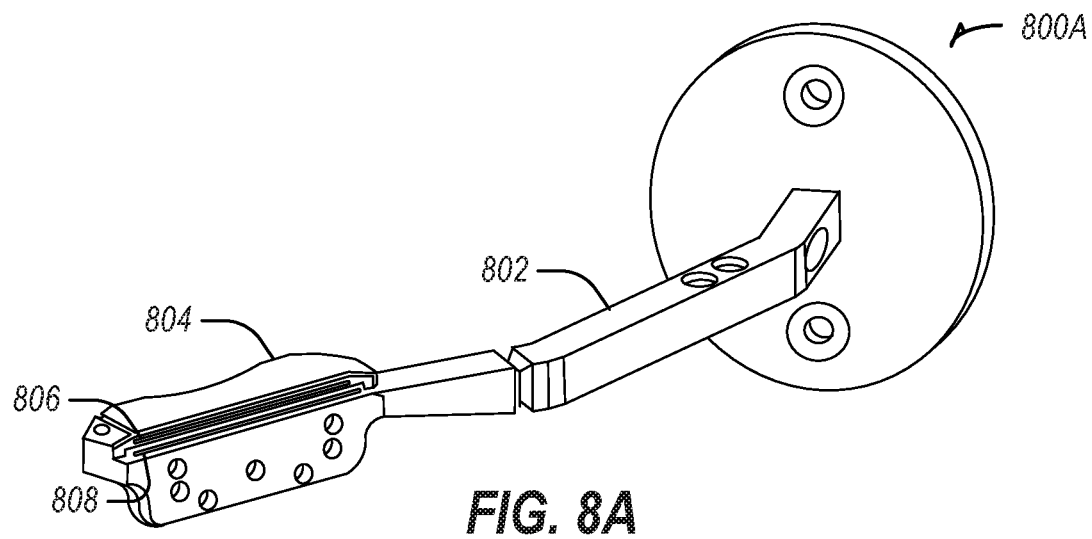
FIGS. 8A-8C illustrate different views of a two slot cut guide in accordance with some embodiments.
Figure 8B:
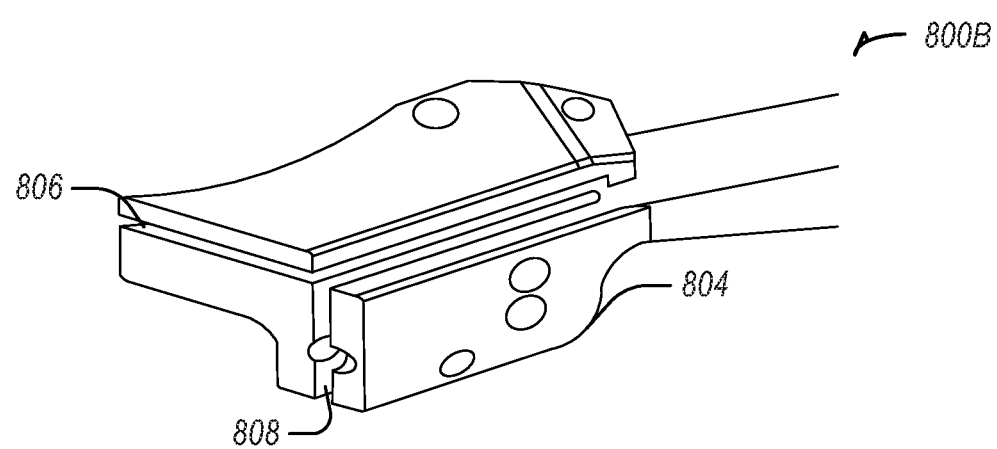
Figure 8C:
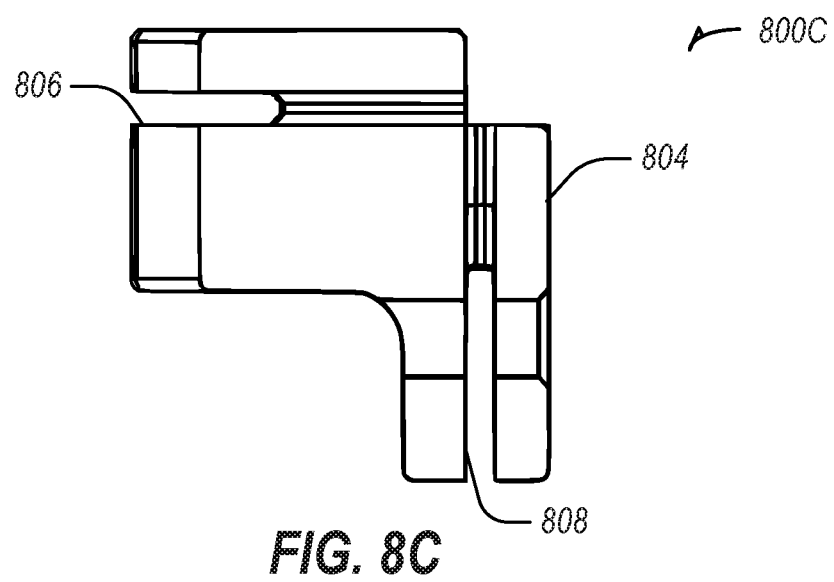

FIGS. 8A-8C illustrate different views 800A-800C of a two slot cut guide 804 in accordance with some embodiments. For example, in FIG. 8A, the two slot cut guide 804 illustrates a view 800A of the two slot cut guide 804 as attached to a robotic arm 802. The two slot cut guide 804 includes a first slot 806 and a second slot 808. The two slots may be perpendicular or substantially perpendicular to each other (e.g., within a few degrees of a right angle).

In FIG. 8B, a view 800B illustrates a close-up and sectioned view where the distal end of the two slot cut guide 804 is cut off to more clearly show the slots 806 and 808. In FIG. 8C, a cross section view is shown of the two slot cut guide 804 including the first slot 806 and the second slot 808.

Figure 9A:
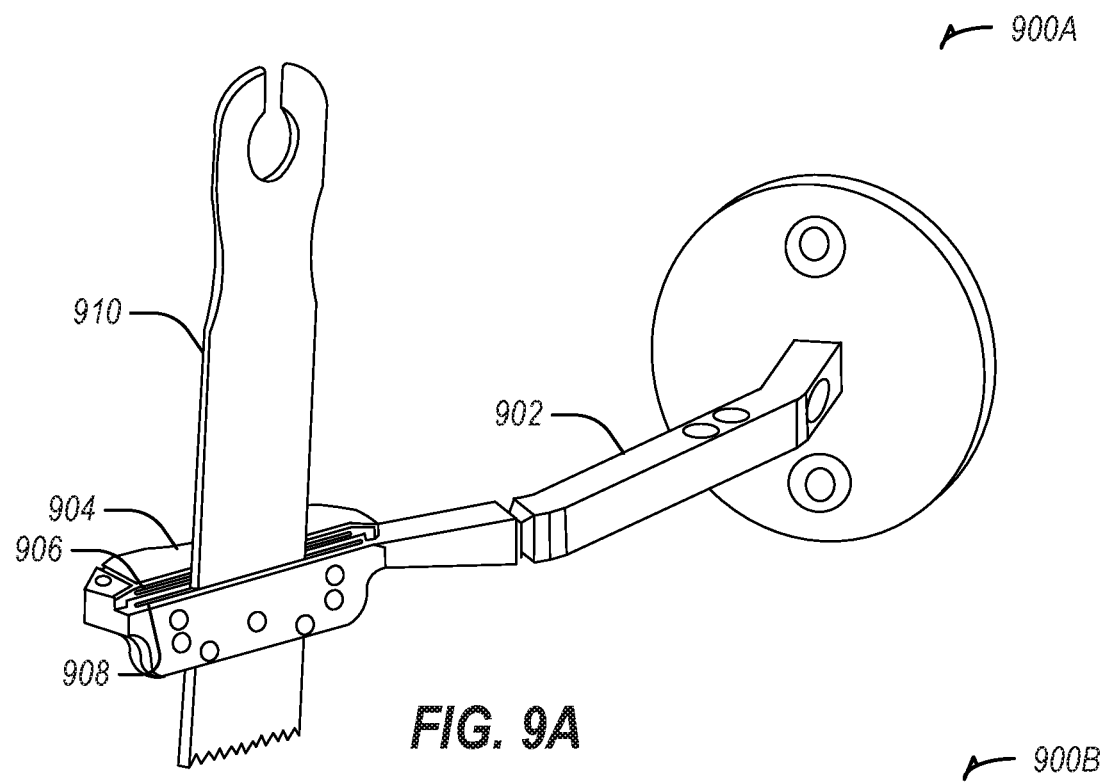
FIGS. 9A-9B illustrate a cutting device used in both slots of a two slot cut guide in accordance with some embodiments.
Figure 9B:
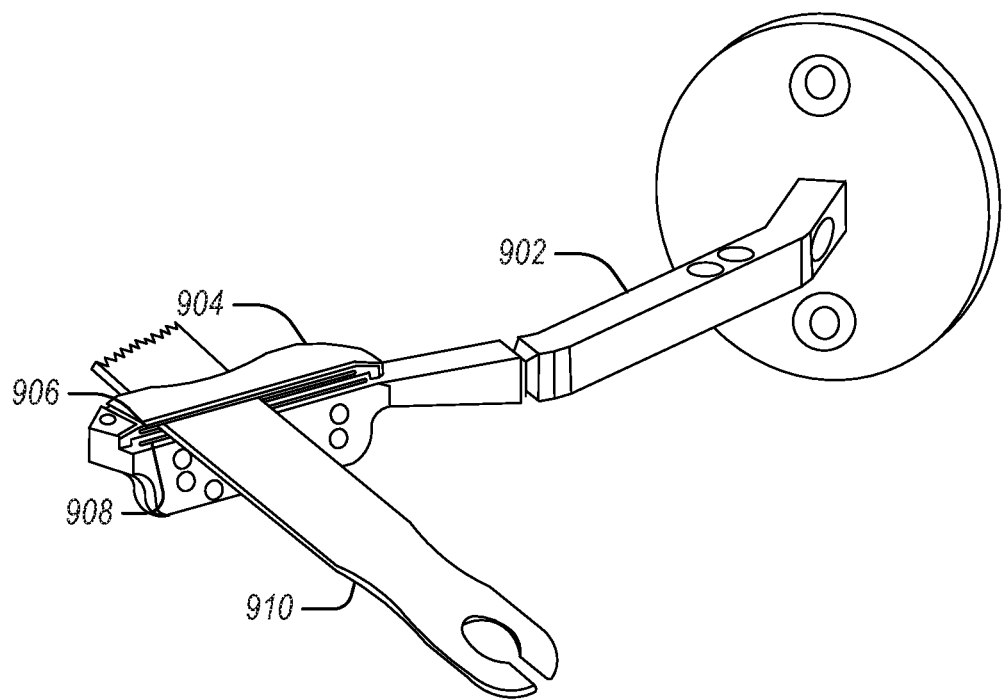

FIGS. 9A-9B illustrate a cutting device 910 used in both slots (906 and 908) of a two slot cut guide 904 in accordance with some embodiments. The two slot cut guide 904 allows the cutting device 910 to be oriented in two different substantially orthogonal orientations without rotation of the cut guide 904 or the robotic arm 902. The two slot cut guide 904 may be affixed to a distal end of a robotic arm 902. FIG. 9A illustrates a first view 900A showing a first orientation of the cutting device 910 in the second slot 908 of the two slot cut guide 904. FIG. 9B illustrates a second view 900B showing a second orientation of the cutting device 910 in the first slot 906 of the two slot cut guide 904. As shown in these two figures, the cutting device 910 may be inserted into either slot of the two slot cut guide 904. The cutting device 910 may also then be removed from a slot of the two slot cut guide 904 and inserted into the other slot. In another example, two different cutting devices may be used for the different slots.

Figure 10A:
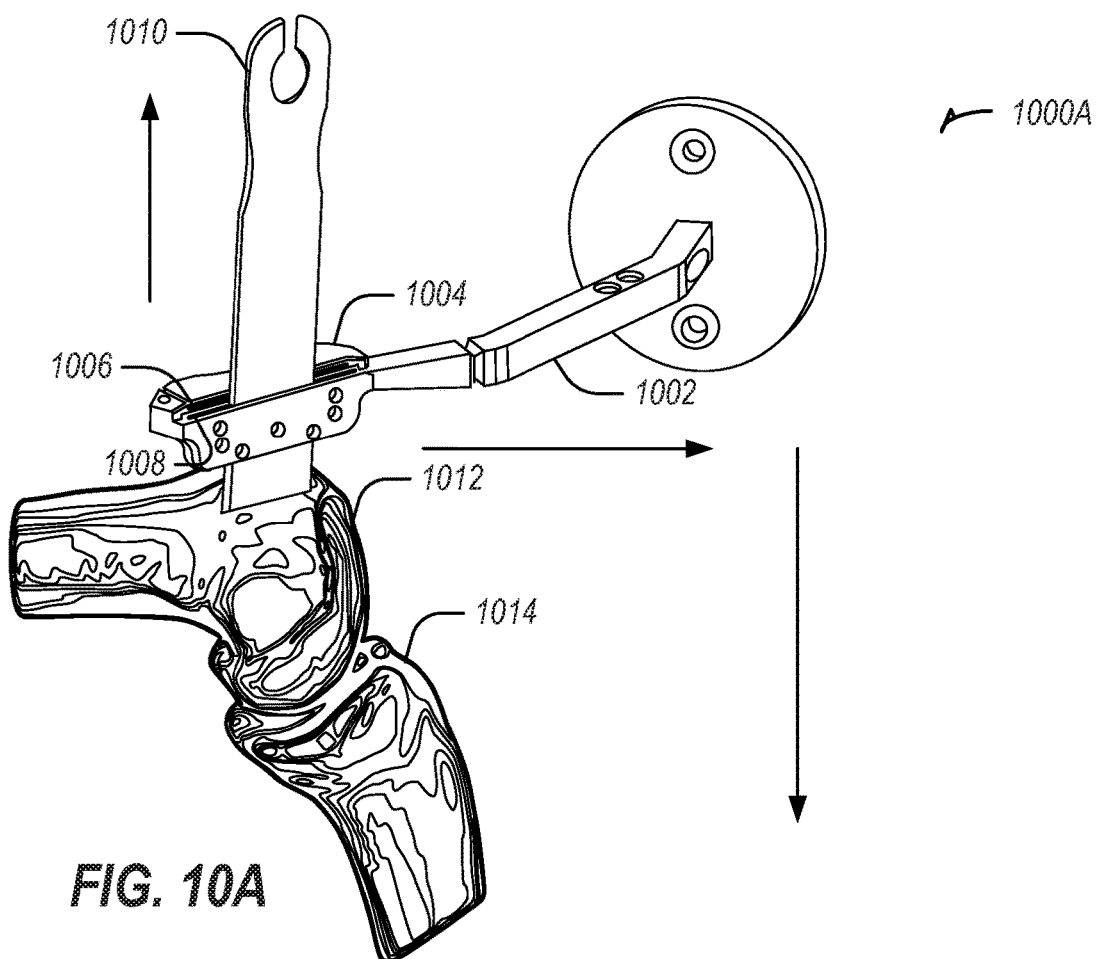
FIG. 10A illustrates a two slot cut guide used to perform a femoral resection in accordance with some embodiments.
Figure 10B:
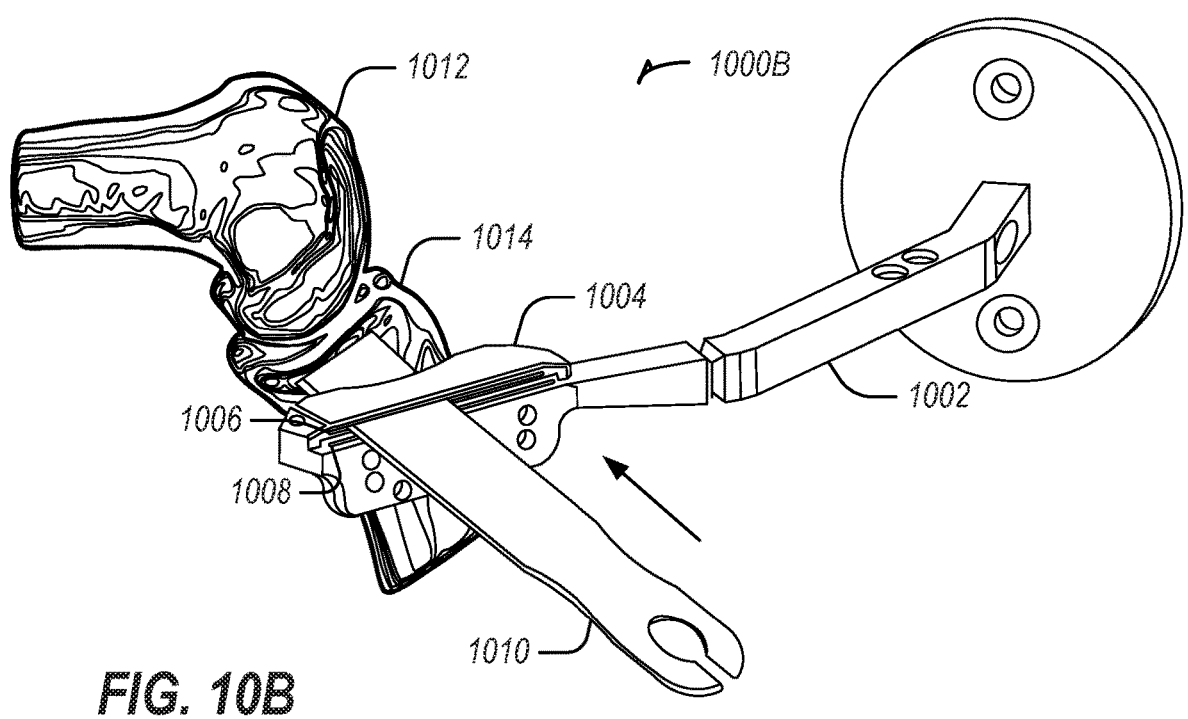
FIG. 10B illustrates a two slot cut guide used to perform a tibial resection in accordance with some embodiments.

FIG. 10A illustrates a two slot cut guide 1004 used to perform a femoral resection in accordance with some embodiments. FIG. 10B illustrates a two slot cut guide 1004 used to perform a tibial resection in accordance with some embodiments. In an example, the two resections may be performed using the same two slot cut guide 1004. The two slot cut guide 1004 may be affixed to a distal end of a robotic arm 1002. FIG. 10A illustrates a first view 1000A showing a first orientation of the cutting device 1010 in the second slot 1008 of the two slot cut guide 1004 to perform a resection of a femur 1012. FIG. 10B illustrates a second view 1000B showing a second orientation of the cutting device 1010 in the first slot 1006 of the two slot cut guide 1004 to perform a resection of a tibia 1014.

In an example, the cutting device 1010 may perform the femoral resection as shown in the first view 1000A, and be removed from the second slot 1008. The robotic arm 1002 may then translate the cut guide 1004 from the position shown in the first view 1000A for the femoral resection to the position shown in the second view 1000B for the tibial resection. The cutting device 1010 may be inserted into the first slot 1006 and the tibial resection may be performed. The translation of the cut guide 1004 by the robotic arm 1002 from the position in the first view 1000A to the position in the second view 1000B may occur without rotation of the cut guide 1004 or the robotic arm 1002, or with only minor rotational adjustments. Allowing the femoral resection and the tibial resection to be performed using a single cut guide with a translation of the two slot cut guide 1004 using the robotic arm 1002 without a substantial rotation allows the procedures to be performed more quickly than if rotation of a cut guide (e.g., a single slot cut guide) were used or if a second cut guide was used. In another example, two different cutting devices may be used for the resections in the two slots, which may still retain the advantages described above with respect to rotation and the two slots. In an example, the procedures may be reversed (e.g., the tibial resection and then the femoral resection).

Figure 11:
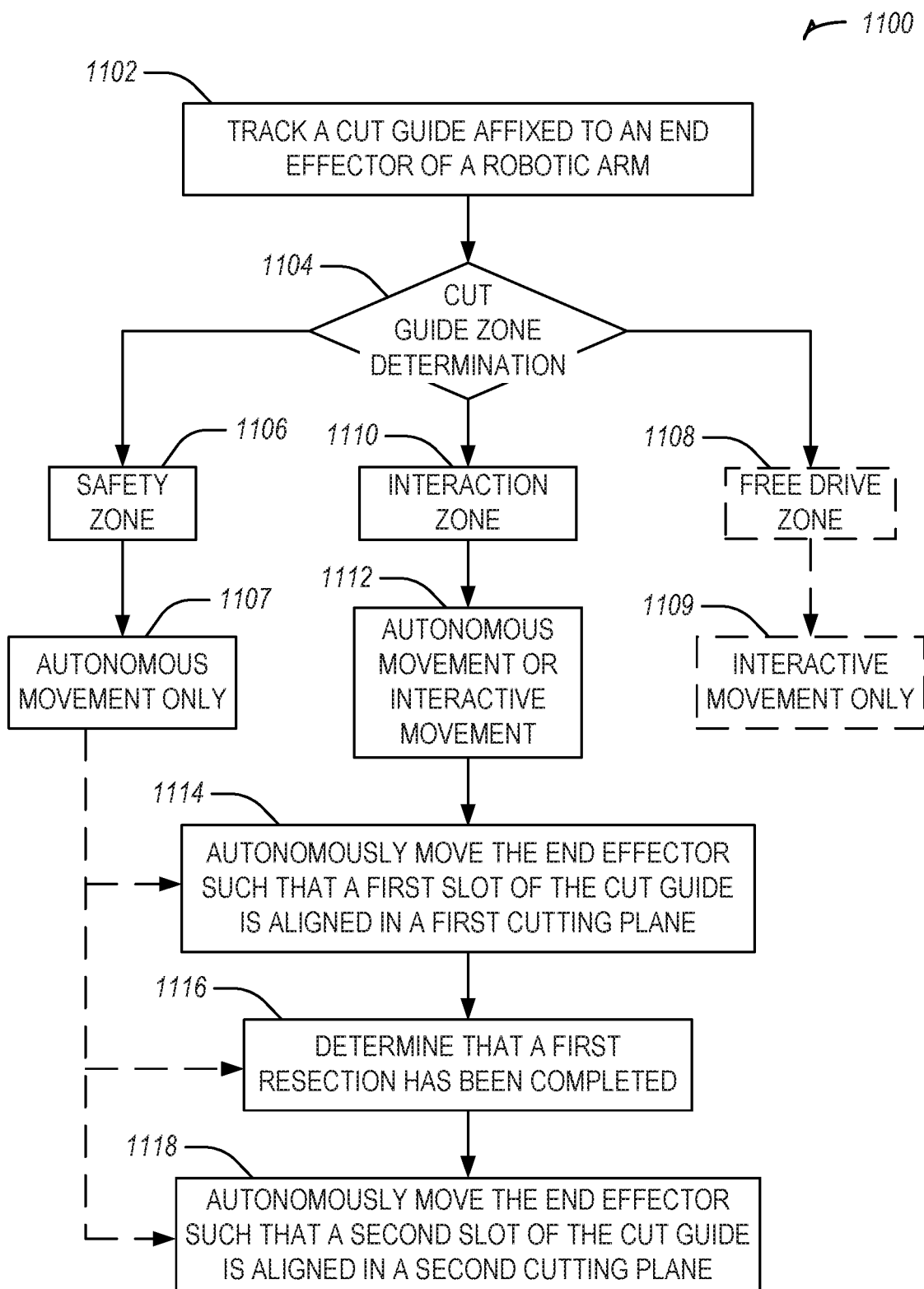
FIG. 11 illustrates a flowchart showing a technique for performing a surgical procedure using a two slot cut guide in accordance with some embodiments.

FIG. 11 illustrates a flowchart showing a technique for 1100 performing a surgical procedure using a two slot cut guide in accordance with some embodiments. The technique 1100 includes an operation 1102 to track a cut guide affixed to an end effector of a robotic arm. The cut guide may include a two slot cut guide or a cut guide with more than two slots.

The technique 1100 includes a decision operation 1104 to perform a cut guide zone determination. In an example, the decision operation 1104 may be performed using a tracking system. For example, a tracking system may be used to track an end effector of a robotic cut guide (e.g., using a robotic controller) and a position or positions of a bone or other patient anatomy (e.g., using an optical tracker). The tracking system may determine where the end effector is relative to aspects of patient anatomy or absolute positions of either or both the end effector and the patient anatomy. When the determination indicates the zone is a safety zone 1106, the technique 1100 includes an operation 1107 to allow autonomous movement only. For example, the robotic arm may resist any movement other than autonomous movement controlled by a robotic controller. An intentional or accidental force, such as by a surgeon, may be resisted or prevented by the robotic arm (e.g., using a counter force initiated by a robotic controller or by simply not enabling movement of any robotic joints). In certain examples, the robotic arm may only be moved through commanded movements. In these examples, the commanded movements may be autonomous or interactive. Within the safety zone the controller may limit commanded movements to only include autonomous movements.

When the determination indicates (optionally) that the zone is a free drive zone 1108, the technique 1100 includes an optional operation 1109 to allow interactive movement only (e.g., prevent the robotic arm from moving autonomously or shutting off power or control to the robotic arm).

In an example, interactive movement may include force applied by the robotic arm, for example in response to an external force (e.g., by a surgeon) on the arm, as a force assist, but may not include autonomous (e.g., without the external force) movement.

When the determination indicates the zone is an interaction zone 1110, the technique 1100 includes an operation 1112 to allow autonomous movement or interactive movement. For example, when an end effector at a distal end of a robotic arm is in the interaction zone 1110, movement may be controlled by a robotic controller or a surgeon manipulating the robotic arm.

The technique 1100 includes an operation 1114 to autonomously move the end effector such that a first slot of the cut guide is aligned in a first cutting plane. Operation 1114 may be performed in response to determining that the interactive movement has caused the cut guide to move into the interaction zone. The end effector may be arranged such that a first slot of the cut guide is aligned in a first cutting plane. In an example, the first cutting plane is a femoral distal cut plane. In an example, the first slot is configured to receive the surgical instrument to perform a femoral distal cut along the first cutting plane. The technique 1100 includes an operation 1116 to determine that a first resection has been completed. The first resection may be completed using a surgical instrument inserted into the first slot of the cut guide.

The technique 1100 includes an operation 1118 to autonomously move the end effector such that a second slot of the cut guide is aligned in a second cutting plane. In an example, the technique 1100 may include determining that a second resection has been completed, may include removing the end effector to the free drive zone 1108 or the interaction zone 1110. In an example, operations 1114, 1116, and 1118 may be initiated only when the robot is within the interaction zone 1110, but may actually take place within the safety zone 1106.

The end effector may be autonomously moved, for example in response to determining that the first resection has been completed. The end effector may be arranged such that a second slot of the cut guide is aligned in a second cutting plane after being autonomously moved (e.g., by the robotic arm controlled by a robotic controller).

In an example, moving the end effector may include aligning the second slot of the cut guide in the second cutting plane, such as by translating the end effector without rotating the end effector. For example, the end effector may be translated without rotating from a position where the first slot of the cut guide was aligned in the first cutting plane to a position where the second slot of the cut guide is aligned in the second cutting plane. In an example, the second cutting plane is a tibial proximal cut plane. The second slot may be configured to receive the surgical instrument (or a second surgical instrument) to perform a tibial proximal cut along the second cutting plane. In another example, the first slot and the second slot are arranged orthogonally to each other on the cut guide.

In an example the term "machine readable medium" may include a single medium or multiple media (e.g., a centralized or distributed database, or associated caches and servers) configured to store one or more instructions. The term "machine readable medium" may include any medium that is capable of storing, encoding, or carrying instructions for execution by a machine and that cause the machine to perform any one or more of the techniques of the present disclosure, or that is capable of storing, encoding or carrying data structures used by or associated with such instructions.

Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Example 1 is a system for surgical tracking and control comprising: a robotic arm configured to allow interactive movement and controlled autonomous movement of an end effector; a cut guide mounted to the end effector of the robotic arm, the cut guide configured to guide a surgical instrument within a plane; a tracking system to determine a position and an orientation of the cut guide relative to a coordinate system; and a control system to: determine a zone occupied by the cut guide using at least the position of the cut guide; in response to determining the zone is a free-drive zone, permit interactive movement of the end effector and prevent autonomous movement of the end effector; and in response to determining the zone is an interaction zone, permit interactive movement and autonomous movement of the end effector.

In Example 2, the subject matter of Example 1 includes, wherein the control system is further to cause, in response to determining the zone is the interaction zone, autonomous movement of the end effector to a cutting position.

In Example 3, the subject matter of Example 2 includes, wherein, after moving to the cutting position, the cut guide is allowed to move along a cut plane and prevented from moving outside of the cut plane.

In Example 4, the subject matter of Example 3 includes, wherein the cut guide is allowed to enter a safety zone while in the cut plane.

In Example 5, the subject matter of Examples 2-4 includes, wherein the control system is to lock the cut guide into the cutting position after causing the cut guide to move to the cutting position.

In Example 6, the subject matter of Example 5 includes, wherein the control system is to move the cut guide relative to a tracked movement of a target object when the cut guide is locked, such that the cut guide is locked into the cutting position relative to the target object.

In Example 7, the subject matter of Examples 5-6 includes, wherein to lock the cut guide into the cutting position, the control system is to lock the cut guide into the cutting position in response to receiving a selection via a user interface.

In Example 8, the subject matter of Examples 2-7 includes, wherein the control system is to lock the cut guide into the cutting position after interactive positioning of the cut guide, the interactive positioning occurring after the autonomous movement.

In Example 9, the subject matter of Examples 2-8 includes, wherein the control system further comprises a user interface, the user interface including a selectable indication that upon selection, causes the control system to autonomously move the cut guide to the cutting position.

In Example 10, the subject matter of Example 9 includes, wherein the cutting position is a predetermined cutting position selected by a surgeon relative to a target object.

In Example 11, the subject matter of Examples 9-10 includes, wherein the control system is to: in response to determining the zone is the free-drive zone, disable the selectable indication; and in response to determining the zone is the interaction zone, activate the selectable indication.

In Example 12, the subject matter of Examples 1-11 includes, wherein the control system is to established the interaction zone using anatomical landmarks of a target bone.

In Example 13, the subject matter of Examples 1-12 includes, wherein the tracking system is further to determine a position and an orientation of a target object relative to the coordinate system.

In Example 14, the subject matter of Example 13 includes, wherein the position and the orientation of the cut guide are determined relative to the position and the orientation of the target object and wherein the coordinate system is determined from the position and the orientation of the target object.

In Example 15, the subject matter of Examples 1-14 includes, wherein the cut guide includes a first slot and a second slot, the first slot and the second slot configured to receive a surgical instrument, and wherein the control system is further to control the robotic arm to navigate the cut guide from a first position within the interaction zone to a second position within the interaction zone, the first position aligning the first slot with a first cut plane and the second position aligning the second slot with a second cut plane.

In Example 16, the subject matter of Example 15 includes, wherein to navigate the cut guide, the control system is to translate the cut guide without rotating the cut guide.

In Example 17, the subject matter of Examples 15-16 includes, wherein the first cut plane is a femoral distal cut plane, wherein the first slot is configured to receive the surgical instrument to perform a femoral distal cut when in the first position, wherein the second cut plane is a tibial proximal cut plane, and wherein the second slot is configured to receive the surgical instrument to perform a tibial proximal cut when in the second position.

In Example 18, the subject matter of Examples 15-17 includes, wherein the first slot and the second slot are arranged orthogonally.

Example 19 is a method for surgical tracking and control, the method comprising: tracking, using a tracking system, interactive movement of an end effector of a robotic arm; determining, using the tracking system, whether the interactive movement has caused a cut guide mounted to the end effector of the robotic arm to move into an interaction zone; receiving an indication to autonomously move the end effector such that the cut guide is aligned in a cutting plane; and autonomously moving, in response to determining that the interactive movement has caused the cut guide to move into the interaction zone, the end effector such that the cut guide is aligned in the cutting plane.

In Example 20, the subject matter of Example 19 includes, locking the cut guide into the cutting plane and moving the cut guide relative to a tracked movement of a target object when the cut guide is locked, such that the cut guide is locked into the cutting plane relative to the target object.

In Example 21, the subject matter of Examples 19-20 includes, determining a trajectory of the cut guide from an interactive force; determining that the trajectory would cause the robotic arm to enter a safety zone; and in response to determining the trajectory would cause the robotic arm to enter the safety zone, preventing movement of the robotic arm into the safety zone.

In Example 22, the subject matter of Examples 19-21 includes, wherein autonomously moving the end effector such that the cut guide is aligned in the cutting plane includes aligning a first slot of the cut guide with the cutting plane; and further comprising: receiving an indication to autonomously move the end effector such that a second slot of the cut guide is aligned in a second cutting plane; and autonomously moving the end effector such that the second slot of the cut guide is aligned in the second cutting plane.

In Example 23, the subject matter of Example 22 includes, wherein the first slot and the second slot of the cut guide are orthogonal, and wherein autonomously moving the end effector such that the second slot of the cut guide is aligned in the second cutting plane includes autonomously translating the end effector from a position within the interaction zone such that the cut guide is aligned in the cutting plane to a position within the interaction zone such that the second slot of the cut guide is aligned in the second cutting plane without rotating the end effector.

Example 24 is at least one machine-readable medium including instructions for operation of a surgical tracking and control system, which executed by a processor, cause the processor to perform operations to: track, using a tracking system, interactive movement of an end effector of a robotic arm; determine, using the tracking system, whether the interactive movement has caused a cut guide mounted to the end effector of the robotic arm to move into an interaction zone; receive an indication to autonomously move the end effector such that the cut guide is aligned in a cutting plane; and autonomously move, in response to determining that the interactive movement has caused the cut guide to move into the interaction zone, the end effector such that the cut guide is aligned in the cutting plane.

In Example 25, the subject matter of Example 24 includes, instructions to present a user interface, the user interface including a selectable indication, which when selected, causes the processor to perform operations to autonomously move the end effector such that the cut guide is aligned in the cutting plane.

In Example 26, the subject matter of Example 25 includes, instructions to: disable, in response to determining the end effector has moved into a free-drive zone, the selectable indication; and activate, in response to determining the end effector has moved into the interaction zone, the selectable indication.

Example 27 is a system for surgical tracking and control comprising: a robotic arm configured to allow interactive movement and controlled autonomous movement of an end effector; a cut guide mounted to the end effector of the robotic arm, the cut guide having a first slot and a second slot, the first slot and the second slot configured to receive a surgical instrument; a tracking system to determine a position and an orientation of the cut guide relative to a coordinate system; and a control system to: control the robotic arm to navigate the cut guide into a first position, and from the first position to a second position, the first position aligning the first slot with a first cut plane and the second position aligning the second slot with a second cut plane.

In Example 28, the subject matter of Example 27 includes, wherein to navigate the cut guide from the first position to the second position, the control system is to translate the cut guide without rotating the cut guide.

In Example 29, the subject matter of Examples 27-28 includes, wherein the first cut plane is a femoral distal cut plane, and wherein the first slot is configured to receive the surgical instrument to perform a femoral distal cut when in the first position.

In Example 30, the subject matter of Examples 27-29 includes, wherein the second cut plane is a tibial proximal cut plane, and wherein the second slot is configured to receive the surgical instrument to perform a tibial proximal cut when in the second position.

In Example 31, the subject matter of Examples 27-30 includes, wherein the first cut plane and the second cut plane are orthogonal.

In Example 32, the subject matter of Examples 27-31 includes, wherein the control system is further to use information captured by a camera to detect that the resection has been completed.

In Example 33, the subject matter of Examples 27-32 includes, wherein the control system is further to: cause, in response to determining the cut guide is in an interaction zone, autonomous movement of the cut guide to the first position using the robotic arm, wherein the first position is within a safety zone.

Example 34 is a method for surgical tracking and control, the method comprising: determining, using a tracking system, whether interactive movement has caused a cut guide mounted to an end effector of a robotic arm to move into an interaction zone; autonomously moving, in response to determining that the interactive movement has caused the cut guide to move into the interaction zone, the end effector such that a first slot of the cut guide is aligned in a first cutting plane; determining that a first resection has been completed using a surgical instrument inserted into the first slot of the cut guide; autonomously moving, in response to determining that the first resection has been completed, the end effector such that a second slot of the cut guide is aligned in a second cutting plane.

In Example 35, the subject matter of Example 34 includes, wherein autonomously moving the end effector such that the second slot of the cut guide is aligned in the second cutting plane includes translating the end effector without rotating the end effector from a position such that the first slot of the cut guide is aligned in the first cutting plane to a position such that the second slot of the cut guide is aligned in the second cutting plane.

In Example 36, the subject matter of Examples 34-35 includes, wherein the first cutting plane is a femoral distal cut plane, wherein the first slot is configured to receive the surgical instrument to perform a femoral distal cut along the first cutting plane, wherein the second cutting plane is a tibial proximal cut plane, and wherein the second slot is configured to receive the surgical instrument to perform a tibial proximal cut along the second cutting plane.

In Example 37, the subject matter of Examples 34-36 includes, wherein the first slot and the second slot are arranged orthogonally to each other on the cut guide.

In Example 38, the subject matter of Examples 34-37 includes, wherein determining that the first resection has been completed includes receiving a user indication that the first resection has been completed.

In Example 39, the subject matter of Examples 34-38 includes, wherein determining that the first resection has been completed includes using information captured by a camera to detect that the resection has been completed.

In Example 40, the subject matter of Examples 34-39 includes, causing, in response to determining the cut guide is in an interaction zone, autonomous movement of the cut guide to the first position using the robotic arm, wherein the first position is within a safety zone.

Example 41 is at least one non-transitory machine-readable medium including instructions for operation of a surgical tracking and control system, which executed by a processor, cause the processor to perform operations to: determine, using a tracking system, whether interactive movement has caused a cut guide mounted to an end effector of a robotic arm to move into an interaction zone; autonomously move, in response to determining that the interactive movement has caused the cut guide to move into the interaction zone, the end effector such that a first slot of the cut guide is aligned in a first cutting plane; determine that a first resection has been completed using a surgical instrument inserted into the first slot of the cut guide; autonomously move, in response to determining that the first resection has been completed, the end effector such that a second slot of the cut guide is aligned in a second cutting plane.

In Example 42, the subject matter of Example 41 includes, wherein to autonomously movie the end effector such that the second slot of the cut guide is aligned in the second cutting plane, the instructions cause the processor to translate the end effector without rotating the end effector from a position such that the first slot of the cut guide is aligned in the first cutting plane to a position such that the second slot of the cut guide is aligned in the second cutting plane.

In Example 43, the subject matter of Examples 41-42 includes, wherein the first cutting plane is a femoral distal cut plane, wherein the first slot is configured to receive the surgical instrument to perform a femoral distal cut along the first cutting plane, wherein the second cutting plane is a tibial proximal cut plane, and wherein the second slot is configured to receive the surgical instrument to perform a tibial proximal cut along the second cutting plane.

In Example 44, the subject matter of Examples 41-43 includes, wherein the first slot and the second slot are arranged orthogonally to each other on the cut guide.

In Example 45, the subject matter of Examples 41-44 includes, wherein to determine that the first resection has been completed, the instructions cause the processor to receive a user indication that the first resection has been completed.

In Example 46, the subject matter of Examples 41-45 includes, wherein to determine that the first resection has been completed, the instructions cause the processor to use information captured by a camera to detect that the resection has been completed.

Example 47 is at least one machine-readable medium including instructions that, when executed by processing circuitry, cause the processing circuitry to perform operations to implement of any of Examples 1-46.

Example 48 is an apparatus comprising means to implement of any of Examples 1-46.

Example 49 is a system to implement of any of Examples 1-46.

Example 50 is a method to implement of any of Examples 1-46.

Method examples described herein may be machine or computer-implemented at least in part. Some examples may include a computer-readable medium or machine-readable medium encoded with instructions operable to configure an electronic device to perform methods as described above. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for surgical tracking and control comprising:
   a robotic arm configured to allow interactive movement and execute controlled autonomous movement of an end effector;
   a cut guide mounted to the end effector of the robotic arm, the cut guide configured to guide a surgical instrument within a plane;
   a tracking system configured to determine a position and an orientation of the cut guide relative to a coordinate system; and
   a control system configured to:
   determine a zone occupied by the cut guide using at least the position of the cut guide;
   in response to determining the zone is a free-drive zone, permit interactive movement of the end effector and prevent autonomous movement of the end effector; and
   in response to determining the zone is an interaction zone, permit interactive movement and execute autonomous movement of the end effector.

2. The system of claim 1, wherein the control system is further configured to cause, in response to determining the zone is the interaction zone, autonomous movement of the end effector to a cutting position.

3. The system of claim 2, wherein, after moving to the cutting position, the cut guide is further configured to be moveable along a cut plane and to be prevented from moving outside of the cut plane.

4. The system of claim 3, wherein the cut guide is further configured to be allowed to enter a safety zone while in the cut plane.

5. The system of claim 2, wherein the control system is further configured to lock the cut guide into the cutting position after causing the cut guide to move to the cutting position.

6. The system of claim 5, wherein the control system is further configured to move the cut guide relative to a tracked movement of a target object when the cut guide is locked, such that the cut guide is locked into the cutting position relative to the target object.

7. The system of claim 5, wherein to lock the cut guide into the cutting position, the control system is further configured to lock the cut guide into the cutting position in response to receiving a selection via a user interface.

8. The system of claim 2, wherein the control system is further configured to lock the cut guide into the cutting position after interactive positioning of the cut guide, the interactive positioning occurring after the autonomous movement.

9. The system of claim 2, wherein the control system further comprises a user interface, the user interface including a selectable indication that upon selection, causes the control system to autonomously move the cut guide to the cutting position.

10. The system of claim 9, wherein the cutting position is a predetermined cutting position selected by a surgeon relative to a target object, the predetermined cutting position aligning a first slot of the cut guide with a cut plane.

11. The system of claim 9, wherein the control system is further configured to:

in response to determining the zone is the free-drive zone, disable the selectable indication; and in response to determining the zone is the interaction zone, activate the selectable indication.

12. The system of claim 1, wherein the control system is further configured to establish the interaction zone using anatomical landmarks of a target bone.

13. The system of claim 1, wherein the tracking system is further configured to determine a position and an orientation of a target object relative to the coordinate system.

14. The system of claim 13, wherein the position and the orientation of the cut guide are determined relative to the position and the orientation of the target object and wherein the coordinate system is determined from the position and the orientation of the target object.

\* \* \* \* \*